(12) United States Patent
Iwase et al.

(10) Patent No.: US 9,574,955 B2
(45) Date of Patent: Feb. 21, 2017

(54) PRESSURE SENSING ELEMENT HAVING AN INSULATING LAYER WITH AN INCREASED HEIGHT FROM THE SUBSTRATE TOWARDS THE OPENING

(71) Applicant: NIPPON MEKTRON, LTD., Tokyo (JP)

(72) Inventors: Masayuki Iwase, Tokyo (JP); Keizo Toyama, Tokyo (JP); Kazuyuki Ozaki, Tokyo (JP); Hirokazu Ohdate, Tokyo (JP); Taisuke Kimura, Tokyo (JP); Ryoichi Toyoshima, Tokyo (JP)

(73) Assignee: NIPPON MEKTRON, LTD., Tokyo (JP)

( * ) Notice: Subject to any disclaimer, the term of this patent is extended or adjusted under 35 U.S.C. 154(b) by 0 days.

(21) Appl. No.: 14/769,290

(22) PCT Filed: Jan. 14, 2015

(86) PCT No.: PCT/JP2015/050817
§ 371 (c)(1),
(2) Date: Aug. 20, 2015

(87) PCT Pub. No.: WO2016/113867
PCT Pub. Date: Jul. 21, 2016

(65) Prior Publication Data
US 2016/0363491 A1    Dec. 15, 2016

(51) Int. Cl.
*G01L 9/12* (2006.01)
*G01L 1/22* (2006.01)
*A61B 5/00* (2006.01)

(52) U.S. Cl.
CPC ............. *G01L 1/2287* (2013.01); *A61B 5/447* (2013.01); *A61B 2562/0247* (2013.01); *A61B 2562/12* (2013.01)

(58) Field of Classification Search
None
See application file for complete search history.

(56) References Cited

U.S. PATENT DOCUMENTS 5,878,620 A    3/1999    Gilbert et al.
6,388,556 B1    5/2002    Imai et al.
(Continued)

FOREIGN PATENT DOCUMENTS

JP    3017968 B2    3/2000
JP    2001-159569 A    6/2001
(Continued)

OTHER PUBLICATIONS

Decision to Grant a Patent dated Jul. 14, 2015, issued in counterpart Japanese application No. 2015-515750, with English Translation. (4 page).

(Continued)

*Primary Examiner* — Harshad R Patel
(74) *Attorney, Agent, or Firm* — Westerman, Hattori, Daniels & Adrian, LLP

(57) ABSTRACT

A pressure sensing element (100) includes a support substrate (11); a sensor electrode (12) supported by the support substrate (11); a pressure sensing film (14) functionalized to be electro-conductive, at least in a portion thereof faced to the sensor electrode (12); and an insulating layer (13) which keeps the sensor electrode (12) and the pressure sensing film (14) apart from each other by a predetermined distance A, and has formed therein an opening (20) in which the sensor electrode (12) is exposed to the pressure sensing film (14), the insulating layer (13) having an aperture wall (13*b*) which partitions the opening (20), and an aperture end (top aperture end (13*a*)) faced to the pressure sensing film (14), and the (Continued)

insulating layer (13) being increased in height, measured from the support substrate (11), continuously towards the opening (20).

14 Claims, 11 Drawing Sheets

(56) References Cited

U.S. PATENT DOCUMENTS

| | | |
|---|---|---|
| 6,531,951 B2 | 3/2003 | Serban et al. |
| 2004/0000195 A1 | 1/2004 | Yanai et al. |
| 2014/0150571 A1 | 6/2014 | Kuniyoshi et al. |

FOREIGN PATENT DOCUMENTS

| | | |
|---|---|---|
| JP | 2002-158103 A | 5/2002 |
| JP | 2002-525564 A | 8/2002 |
| JP | 2004-28883 A | 1/2004 |
| WO | 2012/165082 A1 | 12/2012 |

OTHER PUBLICATIONS

International Search Report dated Feb. 10, 2015, issued in counterpart application No. PCT/JP2015/050817 (1 page).
Written Opinion dated Feb. 10, 2015, issued in counterpart application No. PCT/JP2015/050817 (6 pages).
Decision to Grant a Patent dated Jul. 14, 2015, issued in counterpart Japanese application No. 2015-515750 (1 page).

DIFFERENCE I: HEIGHT H2 − HEIGHT H3
DIFFERENCE II: HEIGHT H6 − HEIGHT H3

PRESSURE SENSING ELEMENT HAVING AN INSULATING LAYER WITH AN INCREASED HEIGHT FROM THE SUBSTRATE TOWARDS THE OPENING

TECHNICAL FIELD

This invention relates to a pressure sensing element, a pressure sensor, and a method of manufacturing a pressure sensing element.

BACKGROUND ART

In recent years, tactile sensing has rapidly been expanding its presence in the fields of medical treatment, welfare, robot, virtual reality, and so forth.

In the automotive field, for example, it has been general to embed a pressure sensing element into a seat. This is aimed at prompting a passenger who gets on a vehicle and sits on the seat to fasten a seat belt. More specifically, upon sitting of the passenger on the vehicle seat, a predetermined level or larger load (weight) is applied to the pressure sensing element. Accordingly, a pressure sensor equipped with the pressure sensing element senses the presence of the passenger, and prompts him or her to fasten the seat belt.

Other expected applications of the pressure sensor include those in medical or nursing field.

More specifically, for example, the pressure sensing element embedded in a mattress of a bed is expected to monitor how the weight of a patient or aged person (also referred to as patient, etc., hereinafter) is applied when he or she lies thereon. By the monitoring, it becomes possible to discover that the patient, etc. has been lying on bed with a fixed posture for a long time. The monitoring enables a third party to know the time to appropriately change the posture of the patient, etc. lying on bed, for bedsore prevention.

It is also possible to use the pressure sensor for a walking aid of the patient, etc. More specifically, if an aged person, while waking with a waking aid, embedded with a pressure sensing element, should lose his or her balance, the pressure sensor can detect the unbalanced weight of the aged person as a change in pressure distribution. It is therefore expected to provide falling prevention for the aged person, or detection of falling. As described above, fields where the pressure sensor may be utilized have been diversified in these years. In particular, the pressure sensor is expected to be mounted on the surface of an article other than flat surface, or to be used in a flexible mode.

There has been proposed a pressure sensing element embodied so that a support substrate having a sensor electrode, and an opposing substrate opposed therewith and having a pressure sensitive resistor, are provided while placing an insulating film in between. In these embodiments, it is important that the sensor electrode and the pressure sensitive resistor, under no load, neither contact nor short-circuit. For this reason, there has been known an embodiment in which the insulating film serves as a spacer for keeping the sensor electrode and the pressure sensitive resistor apart by a predetermined distance.

For example, Patent Literature 1 listed below describes a stacked structure of a pressure sensor in which one circuit board having a sensor electrode provided thereon, and the other circuit board having a pressure sensitive resistor formed thereon by printing, are opposed while placing a spacer sheet in between (see Table 2 in this literature). The spacer sheet is a PET film having tacky layers formed on both surfaces thereof, and on both surfaces of which, the one circuit board and the other circuit board are bonded.

A pressure sensor disclosed in Patent Literature 2 listed below is configured by a resistor board and an electrode support substrate, which are bonded while placing in between a spacer composed of an adhesion layer (see paragraph [0031] of this literature). The literature describes that the adhesion layer is an acrylic tacky film or the like.

A pressure sensor disclosed in Patent Literature 3 listed below is configured by one base film having thereon an electrode, the other base film having thereon a pressure sensitive resistor, and a spacer interposed in between (see FIG. 1 of this literature). Without load, the mutually opposed electrode and the pressure sensitive resistor are kept apart by the thickness of the spacer. The spacer is formed using a resin film, and on both surfaces of which a thermosetting resin adhesive is provided. With the aid of tackiness of the thermosetting resin adhesive, the one base film, the other base film, and the spacer are integrated.

CITATION LIST

Patent Literature

[Patent Literature 1] JP-A-2002-158103
[Patent Literature 2] JP-A-2001-159569
[Patent Literature 3] JP-A-2004-028883

SUMMARY OF THE INVENTION

Technical Problem

The conventional pressure sensors described in Patent Literatures 1 to 3 are provided with the spacer composed of an insulating film as described above. Accordingly, as long as they are used in the flat state, and without load (initial state), the sensor electrode and the pressure sensitive resistor are prevented from being brought into contact and from causing short-circuiting. The conventional pressure sensors have, however, suffered from the problems below.

All spacers used in the conventional pressure sensors are formed by a film of uniform thickness. Accordingly, in order to obtain a good initial detection sensitivity, it is necessary to thin the film, and also to reduce the distance between the sensor electrode and the pressure sensitive resistor (also referred to as "gap", hereinafter). The conventional pressure sensors having such small gaps, when mounted to the surface of an article other than flat surface and used in a flexible mode, has been anticipated to cause short-circuiting in the initial state, since the board bends to make the gap narrower than in the flat state.

On the other hand, the conventional pressure sensor, if configured to have the gap widened enough to prevent short-circuiting even in the bent state, will become difficult to demonstrate a desired level of initial detection sensitivity in the flat state. In short, the conventional pressure sensors have been difficult to demonstrate good initial detection sensitivity both in the flat state and the bent state, as well as to prevent short-circuiting in the initial state. The conventional pressure sensors have therefore not been suitable enough for use in recent wide variety of fields.

This invention was conceived in consideration of the problems described above. More specifically, it is an object of this invention to provide a pressure sensing element capable of demonstrating a good initial detection sensitivity both in the flat state and the bent state, and is prevented from causing short-circuiting in the initial state, as well as a pressure sensor equipped with the pressure sensing element. This invention is also to provide a method of manufacturing a pressure sensing element.

Solution to Problem

According to this invention, there is provided a pressure sensing element which includes a support substrate; a sensor electrode supported by the support substrate; a pressure sensing film functionalized to be electro-conductive, at least in a portion thereof faced to the sensor electrode; and an insulating layer which keeps the sensor electrode and the pressure sensing film apart from each other by a predetermined distance, and has formed therein an opening in which the sensor electrode is exposed to the pressure sensing film, the insulating layer having an aperture wall which partitions the opening, and an aperture end faced to the pressure sensing film, and the insulating layer being increased in height, measured from the support substrate, continuously towards the opening.

According to this invention, there is also provided a pressure sensor which includes the pressure sensing element of this invention; and a detection unit which is electrically connected to the pressure sensing element and detects contact resistance between the pressure sensing film and the sensor electrode.

According to this invention, there is also provided a method of manufacturing a pressure sensing element of this invention, the method includes an electrode forming step, forming a sensor electrode on at least one surface of a support substrate; a coating step, coating a photo-sensitive coating material so as to cover the support substrate and the sensor electrode; an insulating layer forming step, forming an insulating layer by exposing and developing the photo-sensitive coating material, the insulating layer having an opening which is partitioned by an aperture wall and an aperture end, and allows therein the sensor electrode to expose; and a pressure sensing film forming step, forming a pressure sensing film by placing a resin film, functionalized to be electro-conductive, so as to blanket the insulating layer, the coating step which includes a step of coating the photo-sensitive coating material by a screen printing technique, and the insulating layer forming step, succeeding to the coating step, which includes exposing and developing the photo-sensitive coating material, according to the guidelines (1) and (2) below, to thereby form the opening in the insulating layer: wherein guideline (1): increasing the height of the insulating layer, measured from the support substrate, continuously towards the opening; and guideline (2): controlling the in-plane distance between the side wall of the sensor electrode, faced to the aperture wall, and the aperture end in the range from 50 µm or longer and 850 µm or shorter.

Advantageous Effects of Invention

The pressure sensing element of this invention can demonstrate a good initial detection sensitivity both in the flat state and in the bent state, and can prevent short-circuiting in the initial state. It is therefore fully compatible to use in a wide variety of fields.

The pressure sensor of this invention enjoys the advantages of the pressure sensing element of this invention, has a good initial detection sensitivity, and ensures electrical reliability.

The method of manufacturing a pressure sensing element of this invention can easily manufacture the pressure sensing element of this invention.

BRIEF DESCRIPTION OF DRAWINGS

The above and other objects, features and advantages of this invention will be more apparent from the following description of certain preferred embodiments taken in conjunction with the accompanying drawings.

FIG. 9 An explanatory drawing explaining steps of manufacturing the pressure sensing element according to a second embodiment of this invention, wherein

DESCRIPTION OF EMBODIMENTS

Embodiments of this invention will now be explained referring to the attached drawings. In all drawings, all similar constituents will be given the same reference signs to avoid repetitive explanation.

The various constituents of this invention are not always necessarily be independent entities, instead allowing for example that a plurality of constituents are formed as a single member, that a single constituent is formed by a plurality of members, that one constituent forms apart of other constituent, and that a part of one constituent overlaps a part of other constituent.

In this embodiment, membrane, sheet and film are synonymous and are not discriminative, and embrace so-called panel and plate.

In this specification, "initial state" means a state where the pressure sensing film stays unpressurized from outside. "Dynamic range" means the range of change of contact resistance between the sensor electrode and the pressure sensing film. "Initial detection sensitivity" means sensitivity with which the initial pressure sensing load is detected. "Initial pressure sensing load" means a minimum pressurizing force under which electrical conduction in the sensor electrode is detectable, when the pressure sensing film is pressurized from the outside, and the pressure sensing film and the sensor electrode are brought into contact. Now "electrical conduction is detectable" means either that current or voltage not smaller than a predetermined threshold value is detected, or that current or voltage substantially exceeding zero is detected. The smaller the initial pressure sensing load, the higher the initial detection sensitivity, whereas the larger the initial pressure sensing load, the lower the initial detection sensitivity. In general, the initial detection sensitivity preferably falls within a predetermined range. This is because, the detection will be insufficient if the initial detection sensitivity is too low, meanwhile even a very small load unintended for detection may be detected to cause erroneous detection if the initial detection sensitivity is too high.

First Embodiment

Figure 1:
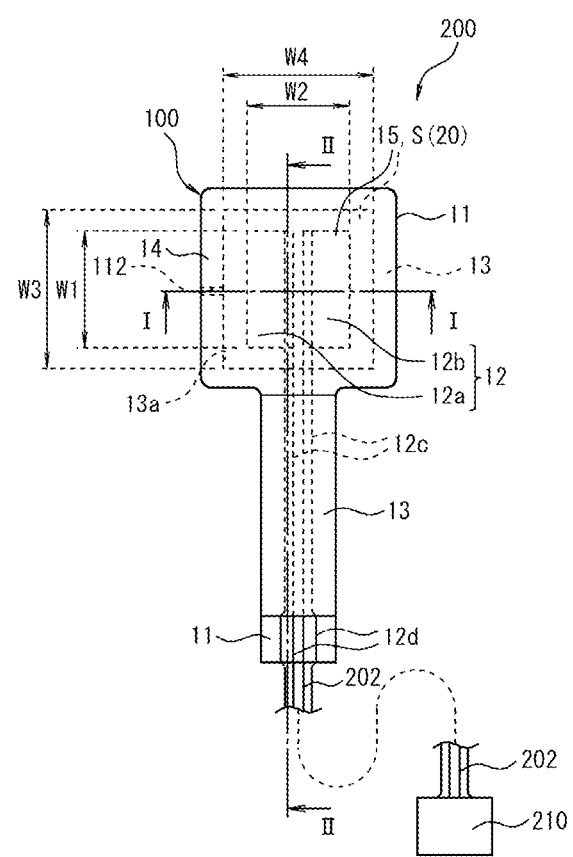
FIG. 1 A plan view illustrating a pressure sensor according to a first embodiment of this invention.
Figure 2A:
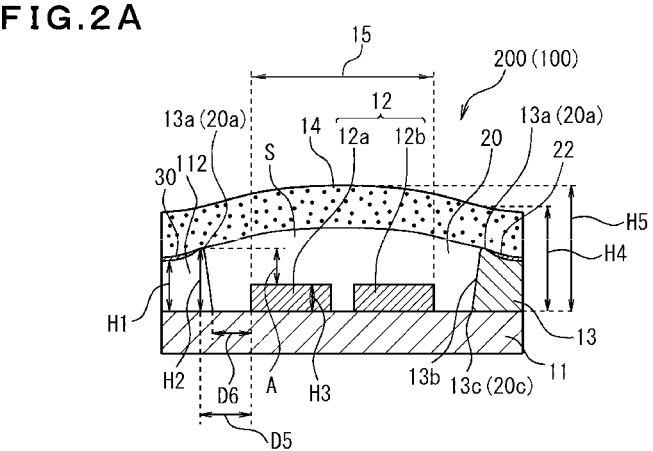
FIG. 2A is a cross sectional view taken along line I-I in FIG. 1.
Figure 2B:
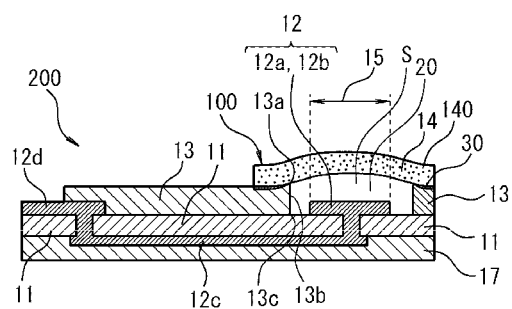
FIG. 2B is a cross sectional view taken along line II-II in FIG. 1.
Figure 3A:
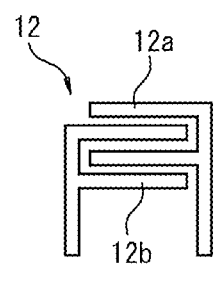
FIG. 3A to FIG. 3C are plan views illustrating a modified example of a sensor electrode.
Figure 3B:
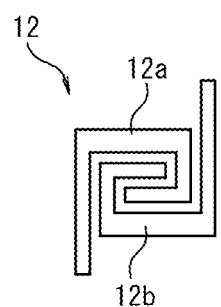
Figure 3C:
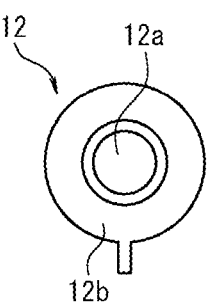
Figure 4:
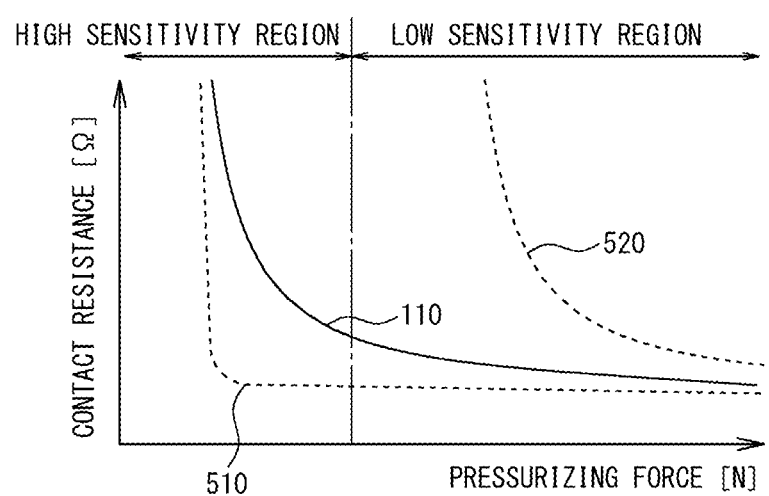
FIG. 4 An explanatory drawing explaining the initial detection sensitivity and dynamic range of the pressure sensing element of the first embodiment.

A pressure sensing element 100 of the first embodiment and a pressure sensor 200 will be explained below, referring to FIG. 1 to FIG. 4. FIG. 1 is a plan view illustrating the pressure sensor 200 according to a first embodiment of this invention. FIG. 2A is a cross sectional view taken along line I-I in FIG. 1, and FIG. 2B is a cross sectional view taken along line II-II in FIG. 1. FIG. 3A to FIG. 3C are plan views illustrating a modified example of a sensor electrode 12. FIG. 4 is an explanatory drawing explaining the initial detection sensitivity and dynamic range of the pressure sensing element 100 of the first embodiment. A curve 110 illustrated in FIG. 4 merely indicates a tendency of the dynamic range of the pressure sensing element 100, without limiting this invention.

The pressure sensing element 100 of this embodiment is a single-channel type element configured by a pressure sensor part 15 having a single sensor electrode 12 and a pressure sensing film 14 opposed to each other.

First, the pressure sensing element 100 and pressure sensor 200 of this embodiment will be outlined.

As illustrated in FIG. 1, FIG. 2A and FIG. 2B, the pressure sensing element 100 has a support substrate 11, the sensor electrode 12 supported on the support substrate 11, a pressure sensing film 14 functionalized to be electro-conductive, at least in a portion thereof faced to the sensor electrode 12, and an insulating layer 13. The insulating layer 13 keeps the sensor electrode 12 and the pressure sensing film 14 apart from each other by a predetermined distance A, and has formed therein an opening 20 in which the sensor electrode 12 is exposed to the pressure sensing film 14. The insulating layer 13 has an aperture wall 13b which partitions the opening 20, and an aperture end (top aperture end 13a) faced to the pressure sensing film 14. The insulating layer 13 is characteristically increased in height, measured from the support substrate 11, continuously towards the opening 20.

Again as illustrated in FIG. 1, the pressure sensor 200 of this embodiment has the pressure sensing element 100, and a detection unit 210 which is electrically connected to the pressure sensing element 100 and detects contact resistance between the pressure sensing film 14 and the sensor electrode 12.

The pressure sensing element 100 of this embodiment is a device, whose measurable physical quantity varies depending on load of pressurizing force from the outside. The pressure sensing element 100, when applied with pressurizing force from the outside, causes changes in the contact resistance between the pressure sensing film 14 and the sensor electrode 12. A first electrode 12a and a second electrode 12b are connected to an unillustrated current source. In the initial state, as illustrated in FIG. 2A and FIG. 2B, the pressure sensing film 14 and the sensor electrode 12 are kept apart, and are not electrically connected. Although not illustrated, when loaded to the pressure sensing film 14 with the pressurizing force from the outside (vertically onto the sheet of drawing), the pressure sensing film 14 deflects towards the sensor electrode 12, comes into contact with the first electrode 12a and the second electrode 12b, and is electrified. The amount of change in the contact resistance in the pressure sensing element 100 correlates with the pressurizing force, and the pressure sensor 200 can quantify the pressurizing force by quantitatively detecting the contact resistance. Although not illustrated, the pressure sensing element 100 may optionally be equipped with a voltage applying unit for applying voltage to the sensor electrode 12.

While being secured with the predetermined distance "A" for keeping the sensor electrode 12 and the pressure sensing film 14 apart (also simply referred to as the "predetermined distance A", hereinafter), the pressure sensing element 100 is successfully prevented from causing short-circuiting when mounted on a flat surface, that is, in the initial state. Note that, the distance A in this invention represents, as illustrated in FIG. 2A, the difference between height H2 of a top aperture end 13a of the insulating layer 13, and height H3 of the sensor electrode 12.

In the pressure sensing element 100, the insulating layer 13 increases in height, measured from the support substrate 11, continuously towards the opening 20. In other words, the surface of the insulating layer 13, opposite to the support substrate 11, has a slope 22 in the vicinity of the opening 20 (see FIG. 2A), which continuously inclines up towards to the opening 20. Accordingly, even if used in a bent state, the pressure sensing element 100 may be successfully prevented from causing short-circuiting.

More specifically, the predetermined distance A for keeping the pressure sensing film and the sensor electrode apart is generally designed small enough to obtain an appropriate level of initial detection sensitivity, so long as the short-circuiting may be prevented in the initial state when the pressure sensing element is mounted on a flat surface. However, the conventional pressure sensing element, having an insulating layer (spacer) composed of a film with a nearly uniform thickness, have been anticipated, when bent, to cause short-circuiting due to a close approach or contact between the pressure sensing film and the sensor electrode.

In contrast, in the pressure sensing element 100, the pressure sensing film 14 which is stacked on the insulating layer 13 having the slope 22 inclines conforming to the slope 22. In addition, in the pressure sensing element 100, the inclination of the surface over the opening 20 is oriented to bulge towards the side opposite to the support substrate 11 (also referred to a "first direction", hereinafter). Accordingly, even if the pressure sensing element 100 is bent in the first direction, the pressure sensing film 14 and the sensor electrode 12 are less likely to approach each other, and thereby the short-circuiting is avoidable. Now, "the surface of the pressure sensing film 14 over the opening 20 is oriented to bulge towards the first direction" includes the case where the pressure sensing film 14 over the opening 20 bulges towards the first direction, and the case where it is kept nearly flat. The case where "the pressure sensing film 14 over the opening 20 bulges in the first direction" may conveniently be referred to the pressure sensing film 14 which appears in FIG. 2A and FIG. 2B or on the right side of FIG. 9D. Meanwhile, the case where "the pressure sensing film 14 over the opening 20 is kept nearly flat" may conveniently be referred to the pressure sensing film 14 which appears in the left side of FIG. 9D. The pressure sensing film 14 having a plurality of openings 20 may have any mode such that it bulges in the first direction over all openings 20, such that it is kept nearly flat over all openings 20, and such that it bulges in the first direction in some place and is kept nearly flat in other place.

The pressure sensing element 100 and the conventional pressure sensing element, assumed to have the same predetermined distance A, will be equally rated with respect to the initial detection sensitivity and short-circuiting, if they are mounted on the flat surface. Meanwhile, when bent in the first direction, the pressure sensing element 100 will be prevented from causing short-circuiting, whereas the conventional pressure sensing element is anticipated to cause short-circuiting.

Moreover, the pressure sensing film 14, the surface of which being oriented to bulge towards the first direction, is less likely to cave into the opening, even if bent in the direction opposite to the first direction (also referred to as a second direction, hereinafter). In conclusion, the pressure sensing element 100 is less likely to cause contact between the pressure sensing film 14 and the sensor electrode 12, even if bent in the second direction, and therefore less likely to cause short-circuiting.

The pressure sensor 200, incorporating the excellent pressure sensing element 100 described above, can enjoy the advantages of the pressure sensing element 100, and can demonstrate excellent durability and electrical reliability. As described above, the pressure sensing element 100 may be prevented from causing short-circuiting, if bent in either the first direction or the second direction. As a consequence, the pressure sensor 200 incorporating the pressure sensing element 100 can show an excellent electrical reliability in both modes such that it is mounted on a curved component, and it is curved when used, proving its full compatibility with use in a wide variety of fields.

The detection unit 210 provided to the pressure sensor 200 optionally includes a power unit (not illustrated) for applying voltage to a voltage applying unit (not illustrated), and a processing unit (not illustrated) for calculating pressurizing force loaded onto the sensor electrode 12 through the pressure sensing film 14. The sensor electrode 12 in this embodiment is configured by combining a pair of the first electrode 12a and the second electrode 12b. When the sensor electrode 12 is applied with pressurizing force through the pressure sensing film 14, the first electrode 12a and the second electrode 12b are electrically connected, and current flows in a lead wire 12c.

Next, the pressure sensing element 100 of this embodiment will be detailed.

As illustrated in FIG. 1, FIG. 2A and FIG. 2B, the pressure sensing element 100 of this embodiment has the support substrate 11 which supports the sensor electrode 12. The support substrate 11 has formed on one surface thereof the sensor electrode 12, and has stacked thereon the insulating layer 13 having the opening 20 formed therein, and the pressure sensing film 14.

The support substrate 11 is any arbitrary substrate so long as it can support the sensor electrode 12 in this embodiment. For example, while the film-like support substrate 11 is used in this embodiment, any arbitrary surface of an article having a form other than film may be used as the support substrate 11. The support substrate 11 is an insulator. The support substrate 11 may be configured, for example, by a flexible member. Accordingly, the pressure sensing element 100 may easily be mounted on a curved surface or on a peripheral surface. In order to use the pressure sensing element 100 while mounting it on a curved surface or a peripheral surface, it is preferable that the support substrate 11 is flexible, and to select a resin film containing carbon particle, as a member for composing the pressure sensing film 14. The pressure sensing film 14 will be described later.

The support substrate 11 in this embodiment is a flexible and insulating film. Materials for composing the insulating film are exemplified by polyethylene, polyethylene terephthalate, polyethylene naphthalate, cycloolefin polymer, polycarbonate, aramid resin, polyimide, polyimide varnish, polyamide-imide, polyamide-imide varnish, and flexible sheet glass, although not limited thereto.

Taking high-temperature durability of the pressure sensor 200 in an environment of use into consideration, preferable materials for composing the support substrate 11 include highly heat-resistant polycarbonate, aramid film, polyimide, polyimide varnish, polyamide-imide, polyamide-imide varnish and flexible sheet glass. If a soldering process is provided for the manufacture of the pressure sensor 200, the materials for composing the support substrate 11 are more preferably any of polyimide film, polyimide varnish film, polyamide-imide film and polyamide-imide varnish film. The thickness of the support substrate 11 typically falls in the range from 12.5 μm or larger and 50 μm or smaller, although not specifically limited. The support substrate 11 of thicker than 12.5 μm will demonstrate an excellent durability in the process of manufacturing or during use of the pressure sensor 200, and that of thinner than 50 μm will demonstrate a good flexibility, ensuring convenient use of the pressure sensing element 100 when mounted on a curved surface, or used in a bent form. The support substrate 11 may be a product preliminarily formed into a sheet as described above, or may be formed by casting or coating, for example, a polyimide-base insulating varnish typically onto a Cu foil as a material of the sensor electrode 12. From the viewpoint, for example, of improving both of the durability and sensitivity characteristic of the pressure sensing element 100, the support substrate 11 is preferably designed to be thicker than the pressure sensing film 14.

Next, the sensor electrode 12 will be explained.

In this embodiment, the sensor electrode 12 is a pair of electrodes disposed side by side, spaced by a predetermined distance in the in-plane direction. The sensor electrode 12 is formed on the support substrate 11, according to a desired pattern. As illustrated in FIG. 1, the sensor electrode 12 in this embodiment is configured by a rectangular first electrode 12a, and a second electrode 12b having substantially the same shape as the first electrode 12a, which are disposed side by side in parallel, and spaced by a predetermined distance. The pattern of the sensor electrode 12 is, however, not limited thereto, instead allowing that, as illustrated in FIG. 3A and FIG. 3B, the first electrode 12a and the second electrode 12b have a comb-like pattern and a spiral pattern, respectively, which mesh with each other. Alternatively, as illustrated in FIG. 3C, the first electrode 12a and the second electrode 12b may be arranged concentrically. More specifically, one of the first electrode 12a and the second electrode 12b has a circular pattern, and the other has a ring pattern surrounding the circular pattern while keeping a predetermined distance in between. The circular pattern includes perfect circle, ellipse and oblong circle.

The space between the opposed first electrode 12a and the second electrode 12b is not specifically limited. For example, if the predetermined distance A between the sensor electrode 12 and the pressure sensing film 14 is 5 μm or larger and 25 µm or smaller, a desired pressure sensing characteristic and stability of manufacture will be well balanced, by determining a design value of the distance as 50 µm or larger and 500 µm or smaller.

The sensor electrode 12 is configured using an electro-conductive member. In this embodiment, the sensor electrode 12 is configured by a low-resistivity metal material. In this embodiment, the surface resistivity of the sensor electrode 12 is smaller than the surface resistivity of the pressure sensing film 14. More specifically, the sensor electrode 12 is preferably composed of, but not limited to, copper, silver, copper- or silver-containing metal material, or aluminum. The form of material may suitably be determined as foil, paste or the like, depending on combination with a method of manufacturing the sensor electrode 12.

The method of manufacturing the sensor electrode 12 is not specifically limited. For example, the sensor electrode 12 is manufactured by patterning a CCL (Copper Clad Laminate) into the first electrode 12a and the second electrode 12b, by photolithographic and etching techniques. Also the lead wire 12c or an external terminal electrode 12d may be formed at the same time in the patterning. The CCL used here is any of a laminate configured by bonding a copper foil, having a desired thickness, to the support substrate 11 using an adhesive or tacky agent; a laminate configured by casting or coating a varnish of an insulating resin onto a copper foil; and a laminate configured by forming a copper foil by wet plating onto the support substrate 11.

While the thickness of the copper foil used in the above-described process is not specifically limited, with the thickness selected within the range from 9 µm or larger and 35 µm or smaller, which is a typical range having been used in the technical field of flexible printed circuit (FPC), the sensor electrode 12 will have a good finish.

From the viewpoint of dimensional accuracy in the thickness or width of the sensor electrode 12, and sensor output characteristic, the sensor electrode 12 composed of a copper foil is preferable. Material for composing the sensor electrode 12 is however not limited to a copper foil, so long as the material can be electrically connected with the pressure sensing film 14 when brought into contact therewith. For example, aluminum foil, silver paste and so forth are usable as the material.

It is preferable that the thus manufactured sensor electrode 12 is further plated in a predetermined region thereof. More specifically, the surface of the sensor electrode 12, faced to the pressure sensing film 14, is plated. By the plating, the sensor electrode 12 may be prevented from being oxidized or degraded, and may be improved in the wear resistance against the pressure sensing film 14 which is repetitively pressed thereon. The plating may be given during, or succeeding to, the filmmaking process of the sensor electrode 12. The plating is specifically exemplified by, but not limited to, nickel plating with a thickness of approximately 2 µm or larger and 10 µm or smaller, and gold plating with a thickness of approximately 0.02 µm or larger and 0.20 µm or smaller.

The height 3H (see FIG. 2A) of such suitably plated sensor electrode 12 typically falls in, but not specifically limited to, the range from 10 µm or larger and 45 µm or smaller, from the practical viewpoint. Height H3 of the sensor electrode 12, and/or, height H2 of the top aperture end 13a in the insulating layer 13, which will be described later, are preferably controlled so that the predetermined distance A may be controlled to a suitable level.

To the first electrode 12a and the second electrode 12b, the lead wires 12c are connected. The lead wires 12c in this embodiment are formed integrally with the first electrode 12a and the second electrode 12b, and are drawn out to the external terminal electrodes 12d. The external terminal electrodes 12d are connected via a flexible wiring 202 to the detection unit 210.

The lead wires 12c in this embodiment are formed, as illustrated in FIG. 2B, so that a part of, or all of, the lead wires 12c are once drawn out through a through hole (TH) onto the surface of the support substrate 11, which is opposite to the surface having the sensor electrode 12 formed thereon. The lead wires 12c drawn out onto the opposite surface are again drawn out, just in front of the external terminal electrode 12d, through a through hole onto the surface having the sensor electrode 12 formed thereon. On such double-sided board having the lead wires 12c disposed on both sides thereof (also simply referred to as "double-sided board", hereinafter), it is easy to form the slope 22 in the vicinity of the opening 20 without being interfered by the lead wires 12c. Accordingly, the double-sided board is more likely to orient the inclination of the surface of the pressure sensing film 14 in the first direction towards the opening 20. According to the double-sided board, the space on the support substrate 11 may be used effectively, to thereby downsize the pressure sensor 200. The double-sided board can also cope with complication of the lead wires 12c, when a plurality of sensor electrodes 12 are provided on a single support substrate 11 to configure a so-called pressure sensor array. As illustrated in FIG. 2B, the double-sided board may optionally have provided thereon a cover 17 which covers and protects the lead wires 12c drawn out onto the opposite surface. The cover 17 is exemplified by, but not limited to, resin cover film typically used as a protective film.

The double-sided board, however, does not limit this invention. The pressure sensing element 100 according to other embodiment, not illustrated, may be a single-sided board on which the lead wires 12c are formed on the same surface with the sensor electrode 12.

Next, the insulating layer 13 will be explained. The insulating layer 13 is provided above the top surface of the support substrate having the sensor electrode 12 formed thereon. The support substrate 11 and the pressure sensing film 14 described later are stacked while placing the insulating layer 13 in between. The insulating layer 13 covers substantially the entire surface of the support substrate 11 and the lead wire 12c (see FIG. 2A and FIG. 2B), but excluding the region where the sensor electrode 12 is formed and the peripheral region, to thereby improve the environmental resistance.

As illustrated in FIG. 2A, the bottom face of the pressure sensing film 14 and the top face of the sensor electrode 12 are kept apart by a distance, larger than the difference between height H2 of the top aperture end 13a of the insulating layer 13, and height H3 of the sensor electrode 12. In other words, the insulating layer 13 serves as a spacer which keeps the sensor electrode 12 and the pressure sensing film 14 apart by a predetermined distance A. In the initial state, by virtue of presence of the insulating layer 13, the sensor electrode 12 and the pressure sensing film 14 are kept apart, so that the sensor electrode 12 is not electrified. The pressure sensor part 15 (see FIG. 1, FIG. 2A and FIG. 2B) is configured by the sensor electrode 12 and the pressure sensing film 14 opposed thereto. Now, "upper" and "lower" in this context mean the directionality when the support substrate 11 is directed downward, and the pressure sensing film 14 is directed upward.

The insulating layer 13 in this embodiment has, as illustrated in FIG. 2A, an aperture wall 13b which partitions the opening 20, the top aperture end 13a which is the aperture end faced to the pressure sensing film 14, and a bottom aperture end 13c faced to the support substrate 11. The opening 20 extends through the insulating layer 13, has an upper aperture 20a faced to the pressure sensing film 14, and has a lower aperture 20c faced to the support substrate 11. The top aperture end 13a is the highest portion of the insulating layer 13 at around the opening 20, when measured from the support substrate 11. A line assumed to connect the top ends of opening 13a at the periphery of the opening 20 agrees with the upper aperture 20a.

The insulating layer 13 increases in height, measured from the support substrate 11, continuously towards the opening 20, and has the slope 22 which inclines upward towards the opening (see FIG. 2A). Accordingly, height H2 of the top aperture end 13a is larger than height H1 of the insulating layer 13 measured at an arbitrary point more significantly apart from the opening 20 than the top aperture end 13a.

Provision of the slope 22 only at least in a part of the circumference of the opening 20 will suffice. The slope 22 is preferably formed in two opposing directions while placing the opening 20 in between, and more preferably in four directions centered round the opening 20. For example, the slope 22 may be formed in four directions which cross substantially at right angles centered round the opening 20, or may be formed substantially in radial directions centered round the opening 20.

While methods of forming the insulating layer 13 are not specifically limited, the insulating layer 13 having the opening 20 formed therein may be formed, for example, by coating a photo-sensitive coating material 174 by a printing technique over the support substrate 11 having the sensor electrode 12 provided thereto, followed by exposure and development. In this process, the slope 22 may be formed to a certain level of significance by controlling the viscosity of the photo-sensitive coating material 174, prompt exposure after the coating by printing, exposure conditions and so forth. In other words, unless these conditions are properly controlled, the photo-sensitive coating material 174 formed by printing would be leveled, and would fail in producing a desired amount of variation in the level of height of the insulating layer 13. The insulating layer 13 may be formed by a technique other than printing. For example, a film material having the opening 20 preliminarily formed at a predetermined position, and embossed to form projections around the opening 20 may be used as the insulating layer 13, and may be bonded to the support substrate 11.

The dimension of the aperture of opening 20 may suitably be determined, without departing from the spirit of this invention. For example, with respect to the pressure sensor part 15 with a longitudinal dimension W1 of 4.0 mm, and a transverse dimension W2 of 2.5 mm illustrated in FIG. 1, the top aperture end 13a can be designed to have a longitudinal dimension W3 of 4.2 mm, and a transverse dimension W4 of 2.7 mm or around. The pressure sensor part 15 is disposed at the center of the top aperture end 13a. In-plane distance D5 between the side wall of the sensor electrode 12, faced to the aperture wall 13b, and the top aperture end 13a (see FIG. 2A) is preferably designed to be 0.05 mm or larger in all directions. With this design, taking the positional accuracy of the opening 20 in the manufacture into consideration, the insulating layer 13 is prevented from overlapping with the sensor electrode 12, and thereby the yield of the pressure sensing element 100 may be improved. Now, the in-plane distance means the distance between the side face of the sensor electrode 12 faced to the aperture wall 13b, and the top aperture end 13a, observed in a plan view of the pressure sensing element 100. The wording of "longitudinal" and "transverse", described above in relation to the dimensions of the pressure sensor part 15 and the top aperture end 13a, are used here to indicate the directions merely for the convenience, and does not limit this invention.

As illustrated in FIG. 2A and FIG. 2B, the aperture end (top aperture end 13a) is rounded. In other words, the edge of the insulating layer 13 which surrounds the upper aperture 20a of the opening 20 is chamfered, and is suitably rounded. With such configuration, the pressure sensing film 14 which covers the opening 20 is prevented from friction with the top aperture end 13a, even when pressed towards the sensor electrode 12. According to this embodiment, the pressure sensing film 14 may be improved in durability against repetitive use.

In the pressure sensing element 100 of this embodiment, as illustrated in FIG. 2A, the aperture wall 13b slopes from the top aperture end 13a down to the bottom aperture end 13c. The angle of inclination of the aperture wall 13b away from the support substrate is larger than the angle of inclination of the slope 22 away from the support substrate 11.

In this embodiment, the in-plane distance (distance D5, see FIG. 2A) between the side face of the sensor electrode 12 faced to the aperture wall 13b and the aperture end (top aperture end 13a) is 50 μm or longer and 850 μm or shorter. With distance D5 in the pressure sensing element 100 controlled in the above-described range, a suitable aperture of the opening 20 may be determined, and the slope 22 may be provided to the insulating layer 13.

The in-plane distance (distance D6, see FIG. 2A) between the side wall of the sensor electrode 12 faced to the aperture wall 13b and the bottom aperture end 13c preferably exceeds zero. In other words, the insulating layer 13 and the sensor electrode 12 are kept apart, rather than brought into contact. D6 is preferably not longer than D5.

Figure 9A:
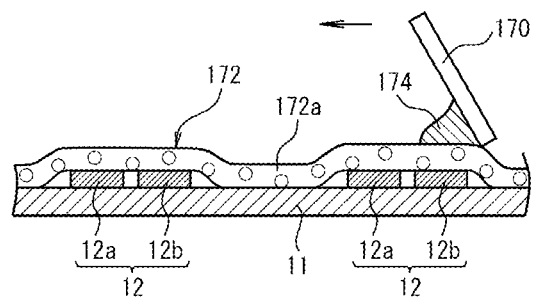
FIG. 9A illustrates a step of coating of photo-sensitive coating material by screen printing over a support substrate having sensor electrodes provided thereto.

The insulating layer 13 may be formed using a photo-sensitive material, and by techniques of screen printing, exposure, and development. More specifically, the sensor electrode 12 having a height H3 of 10 μm or larger and 45 μm or smaller is formed on the top surface of the support substrate 11, and a general screen printing plate 172 is placed so as to cover the sensor electrode 12 (see FIG. 9A). Investigations by the present inventors revealed that the screen printing plate 172 was lifted off above the support substrate 11 in the vicinity of the sensor electrode 12, and was landed on the support substrate 11 at positions approximately 1 mm away from the side faces of the sensor electrode 12. In FIG. 9A, a plurality of circles seen inside the screen printing plate 172 represent cross sections of thin stainless steel wires composing the mesh. By coating in this state the photo-sensitive coating material 174 over the support substrate 11, it is now possible to form in the insulating layer 13 the slope 22 which extends up to a point approximately 1 mm away from the side faces of the sensor electrode 12 faced to the aperture wall 13b. Accordingly, by controlling distance D5 to 850 μm or shorter, the slope 22 may surely be formed in the region containing distance D5. Meanwhile, with distance D5 controlled to 50 μm or longer, development failure will be avoidable, and even in case of accidental misalignment in the exposure process, the sensor electrode 12 and the insulating layer 13 may be prevented from overlapping with each other.

In the pressure sensing element 100 of this embodiment, the difference (distance A) between height H2 of the aperture end (top aperture end 13a) and height H3 of the sensor electrode 12, both measured from the support substrate 11, is preferably 5 µm or larger and 25 µm or smaller. With such configuration, the pressure sensing element 100 is successfully prevented from causing short-circuiting in the initial state both in the flat state and in the bent state.

Now, in the pressure sensing element 100, since the insulating layer 13 has the slopes 22 formed therein, so that the smaller the aperture size, the higher the top aperture end 13a, whereas the larger the aperture size, the lower the top aperture end 13a. With the above-described distance D5 controlled within the above-described range, the difference (distance A) may easily be designed in the range from 5 µm to 25 µm.

By controlling the predetermined distance A and distance D5 in the preferable ranges, the pressure sensing element 100 can exhibit excellent performances both in terms of initial detection sensitivity and dynamic range, as indicated by the curve 110 in FIG. 4. For example, when externally applied with a pressurizing force of 4.4 N (ca. 450 gf) onto the pressure sensing film 14, the pressure sensing element 100 can achieve a dynamic range of contact resistance of 500Ω to 2500Ω. In FIG. 4, the 110 indicates tendencies of the dynamic range and the initial detection sensitivity of the pressure sensing element 100, and a curve 510 and a curve 520 indicate undesirable tendencies of the dynamic range and the initial detection sensitivity. The ordinate represents the contact resistance [Q] between the pressure sensing film 14 and the sensor electrode 12, and the abscissa represents the pressurizing force [N]. The ordinate is a logarithmic scale.

As illustrated in FIG. 1, FIG. 2A and FIG. 2B, by stacking the pressure sensing film 14 over the insulating layer 13 having the opening 20 formed therein, the opening 20 configures a hollow space S. The insulating layer 13 may optionally have formed therein a vent hole 112 through which the hollow space S and the outside of the pressure sensing element 100 can communicate (see FIG. 1 and FIG. 2A). With the vent hole 112, the pressure sensing element 100 can clear the difference between the inner pressure of the hollow space S and the external pressure. While the widthwise dimension of the vent hole 112 is not specifically limited, when given a widthwise dimension of 50 µm or larger and 500 µm or smaller, the vent hole 112 can fully demonstrate the pressure control function. While the height of the vent hole 112 is again not specifically limited, when given a height equivalent to the thickness of the insulating layer 13, the vent hole 112 can be formed at the same time with the opening 20, taking an advantage in terms of productivity. Alternatively, the insulating layer 13, when configured with a highly breathable insulating material, can demonstrate such pressure control function without being provided with the vent hole 112. The hollow space S houses the sensor electrode 12.

While the insulating material composing the insulating layer 13 is not specifically limited, the opening 20 may be formed accurately by exposure and development, using a photo-sensitive material such as photo-sensitive sheet or photo-sensitive coating material. In particular, the insulating layer is advantageously formed by coating the photo-sensitive material by screen printing over the support substrate 11 so as to cover the sensor electrode 12, followed by exposure of a predetermined portion to form the opening 20.

The insulating layer 13 may alternatively be formed by aligning and bonding a tacky sheet or adhesive sheet, having preliminarily formed therein the opening 20 and the slope 22 which surrounds the opening 20, to the top surface of the support substrate 11.

While the insulating material for composing the insulating layer 13 is not specifically limited, use of a photo-sensitive material such as a photo-sensitive sheet or photo-sensitive coating material is advantageous in terms of accurately forming the opening by exposure and development. The insulating layer 13 may alternatively be formed by aligning and bonding a tacky sheet or adhesive sheet, having preliminarily formed therein the opening 20, to the top surface of the support substrate 11.

The photo-sensitive material is exemplified by an epoxy-base resin given an appropriate level of flexibility by a known technique such as urethane modification. By using such epoxy-based resin, the insulating layer 13 having an appropriate level of flexibility and heat resistance durable against reflow process, may be formed.

Height H2 of the top aperture end 13a of the insulating layer 13, measured from the surface of the support substrate 11, preferably falls in the range from 15 µm or larger and 70 µm or smaller, and is more preferably 15 µm or larger and 40 µm or smaller. By designing height H2 of the top aperture end 13a as 70 µm or smaller, light which is illuminated in the process of exposure for forming the opening 20 can reach deep inside the photo-sensitive material, and thereby the opening 20 is formed accurately. In order to further improve the exposure sensitivity in the process of forming the insulating layer 13, the photo-sensitive material is preferably given in a semi-transparent form, having a total light transmittance of 30% or larger.

The opening 20 in this embodiment has a rectangular shape as stacked in FIG. 1. However, the shape of the opening 20 may suitably be altered to circular, polygonal or undefined shape, depending on the shape of the sensor electrode 12 housed therein.

Over the insulating layer 13, the pressure sensing film 14 is laminated. In this embodiment, the insulating layer 13 and the pressure sensing film 14 are bonded while placing an adhesion layer 30 in between. Any of tacky agent, adhesive, tacky sheet and adhesive sheet may be used for the adhesion layer 30, so long as it can bond the insulating layer 13 and the pressure sensing film 14. The adhesion layer 30 preferably has substantially the same aperture pattern of the opening 20, so as not to affect the contact resistance between the sensor electrode 12 and the pressure sensing film 14. For example, the adhesion layer 30 may be provided on either the insulating layer 13 or the pressure sensing film 14, and then bond the other onto the one while properly aligned.

In the pressure sensing element 100 of this embodiment, the surface of the insulating layer 13 faced to the pressure sensing film 14, and the pressure sensing film 14, are fixed to each other while placing the adhesion layer 30 in between, and the surface of the insulating layer 13 faced to the support substrate 11 is fixed to the support substrate 11 without placing the adhesion layer 30 in between. This embodiment may be achieved by forming, through printing, the insulating layer 13 directly onto the support substrate 11. By forming, through printing, the insulating layer 13 onto the support substrate 11, a risk of misalignment which is anticipated in the process of bonding the film is markedly reduced, and thereby the pressure sensing element 100 may be manufactured with a high yield.

The pressure sensing film 14 is a component which is brought into contact with the sensor electrode 12, to electrify the pair of the first electrode 12a and the second electrode 12b, which configure the sensor electrode 12. "The pressure sensing film 14 is functionalized to be electro-conductive" means that the pressure sensing film 14 is electro-conductive, only enough to electrify the sensor electrode 12 through the pressure sensing film 14 when pressed externally. More specifically, the pressure sensing film 14 which is externally loaded by pressurizing force is brought into contact with the first electrode 12a and the second electrode 12b so as to bridge them, and thereby the first electrode 12a and the second electrode 12b are electrically connected.

In the configuration of this embodiment, as illustrated in FIG. 2A and FIG. 2B, height H5 of the pressure sensing film 14 at the point opposed to the center of the opening 20, when measured from the support substrate 11, is larger than height H4 of the pressure sensing film 14 at the point opposed to the aperture end (top aperture end 13a). In other words, the pressure sensing film 14 which covers the opening 20 bulges towards the direction opposite to the support substrate 11. According to this embodiment, the short-circuiting in the initial state is successfully avoidable, even if the pressure sensing element 100 is bent in the first direction or second direction. Considering now that the pressure sensing element 100 may occasionally be mounted in the direction other than the horizontal direction, height H5 and height H4 are preferably compared using the respective values measured under an environment from which any effect of their own weights are eliminated.

The pressure sensing film 14 in this embodiment will suffice if it is functionalized to be electro-conductive, only enough to electrify the sensor electrode 12 when brought into contact therewith.

The pressure sensing film 14 in this embodiment is a resin film containing a carbon particle 140, as illustrated in FIG. 2A and FIG. 2B. The pressure sensing film 14 is functionalized to be electro-conductive with the carbon particle 140. In other words, the resin film used as the pressure sensing film 14 contains just as much amount of the carbon particle 140 necessary for demonstrating an electro-conductive function. The resin film is flexible. With such electro-conductive function of the resin film per se, the pressure sensing film 14 may be thinned, a good flexibility is ensured, and the dynamic range of the pressure sensing element 100 may be increased. Since the electro-conductive resin film is used as the pressure sensing film 14, so as to configure the touch area, so that the pressure sensing film 14 is less likely to make the user, who externally touches it, feel like something is wrong.

The description above is by no means limit this invention, and allows a modified example in which the pressure sensing element 100 uses the pressure sensing film 14 having a pressure sensitive resistor in a predetermined area of a surface of a resin film. The pressure sensitive resistor may be obtained by printing a carbon paste onto the resin film, or by depositing thereon a semiconductor material such as copper sulfide or copper oxide by evaporation.

The resin film composing the pressure sensing film 14 may be configured by using any known resin, without departing from the spirit of this invention. The resin is specifically exemplified by polyesters such as polyethylene terephthalate, polyethylene naphthalate and cyclic polyolefin; polycarbonate; polyimide; polyamide-imide; and liquid crystalline polymer. These resins may be used independently, or in a mixed form of two or more species thereof, to configure the pressure sensing film 14.

From a special point of view that the pressure sensing element 100 may suitably be provided with heat resistance, the pressure sensing element 100 preferably uses polyimide or polyamide-imide as a major constituent. The resin film mainly composed of polyimide or polyamide-imide may have a heat resistance of 260° C. or above. The major constituent means a resin which accounts for 50% by mass or more, preferably 70% by mass or more, and particularly 90% by mass more, relative to 100% by mass of the resin composing the pressure sensing film 14. For example, as the resin contained in the pressure sensing film 14, either polyimide or polyamide-imide, or a combination thereof may substantially account for 100% by mass.

The carbon particle 140 contained in the pressure sensing film 14 is a component for imparting electro-conductivity to the pressure sensing film 14. The carbon particle 140 is a particulate carbon material, and is exemplified by any one species of, or combination of two or more species of, acethylene black, furnace black (Ketjenblack), channel black, and thermal black, but is not limited thereto.

The content of the carbon particle 140 in the pressure sensing film 14, and shape and size of the carbon particle 140 are not specifically limited without departing from the spirit of this invention. They may suitably be determined, so long as the sensor electrode 12 may be electrified upon contact between the pressure sensing film 14 and the sensor electrode 12.

The thickness of the pressure sensing film 14 is preferably 6.5 μm or larger and 40 μm or smaller. With a thickness of 6.5 μm or larger, the pressure sensing film 14 is proven to be durable. Meanwhile with a thickness of 40 μm or smaller, the pressure sensing film 14 can ensure a good initial detection sensitivity when pressurized, and a large dynamic range.

The thickness of the pressure sensing film 14 may be measured by using a general height gauge, upright gauge or other thickness measurement means.

The pressure sensing film 14 preferably has a surface resistivity of 7 kΩ/sq or larger and 30 kΩ/sq or smaller. With the surface resistivity controlled in the above described range, the pressure sensing film 14 will show a small variation in the sensor resistivity when applied with a large load, and can ensure a high electrical reliability. As a rough indication, the large load is now defined as approximately 1.1 MPa (typically achieved by applying a pressurizing force of 450 gf onto a 4 $mm^2$ pressure sensor part 15).

With the surface resistivity controlled in the above-described range, the initial detection sensitivity will be good as indicated by the curve 110 in FIG. 4, and this contributes to achieve a large dynamic range. More specifically, the pressure sensing element 100 is now possibly designed to show the initial detection sensitivity in a high sensitivity region of 0.25 MPa or below, and further 0.17 MPa or below, and to show a moderate change in the sensor output ranging from the initial detection load to the maximum load of pressurizing force.

The predetermined range of the surface resistivity of the pressure sensing film 14 may be controlled by the amount of mixing of the carbon particle 140 contained in the pressure sensing film 14. In other words, the amount of mixing of the carbon particle 140 contained in the pressure sensing film 14 may be determined so as to adjust the surface resistivity of the pressure sensing film 14 within the above-described range.

In a film-like article such as the pressure sensing film 14, electric current mainly flows along the surface of the film-like article. For this reason, the resistivity of the film-like article in this specification is defined by sheet resistance per unit area while neglecting the thickness-wise dimension. The unit is specifically denoted as Ω/☐, or Ω/sq.

The pressure sensing element 100 may be controlled so that the surface of the pressure sensing film 14, faced to the sensor electrode 12, has a surface roughness Rz of 0.10 µm or larger and 0.50 µm or smaller. By such control, a good formability of the pressure sensing film 14 is ensured, and detection sensitivity of contact resistance is stabilized.

The surface roughness Rz of the pressure sensing film 14 may be measured using a general surface roughness tester, or by surface roughness analysis under a laser microscope. The general surface roughness tester is exemplified by four-probe measuring instrument, and specifically exemplified by resistivity meter available from Mitsubishi Chemical Analytech Co., Ltd., but not limited thereto.

The pressure sensing film 14 preferably has a Young's modulus of 5 GPa or smaller. This ensures a sufficient flexibility to the pressure sensing film 14. With the Young's modulus controlled in the above described range, it is now possible to successfully quantify changes in the contact resistance with increase in the pressurizing force applied to the pressure sensing film 14, within the above-described ranges of the predetermined distance A, and the aperture size of opening 20.

Method of forming the resin film containing the carbon particle is not specifically limited. The resin film may typically be formed by mixing the carbon particle 140 with one species, or two or more species of resins, which serve as source materials, properly mixing them, and by casting the mixture into a film.

The pressure sensor 200 equipped with the above-described pressure sensing element 100 is excellent in flexibility, high sensitivity characteristic and electrical reliability, and is versatile for various applications. For example, the pressure sensing element 100 may be attached to the surface of an arbitrary object, and may be used for a simple measurement for sensing pressure exerted on the surface. In particular, the pressure sensing element 100 may be attached to a curved surface such as bent surface or spherical surface, to be subjected touch operation, and also may be made operable while being switched among various functions depending on magnitude of the pressurizing force. It is advantageous not only in that it allows touch operation on a two-dimensional plane like in the conventional touch panel, but also in that it is applicable to electronic whiteboard or electronic paper which is used as a user interface allowing three-dimensional input.

Second Embodiment

Next, a pressure sensing element 300 and a pressure sensor 400 according to a second embodiment of this invention will be explained referring to FIG. 5 to FIG. 8, and occasionally referring to FIG. 9D. The pressure sensing element 300 of this embodiment is different from the pressure sensing element 100 of the first embodiment, in that it has a plurality of sensor electrodes 12. The pressure sensor 400 is different from the pressure sensor 200 in that it has a pressure sensing element 300 in place of the pressure sensing element 100.

Figure 5:
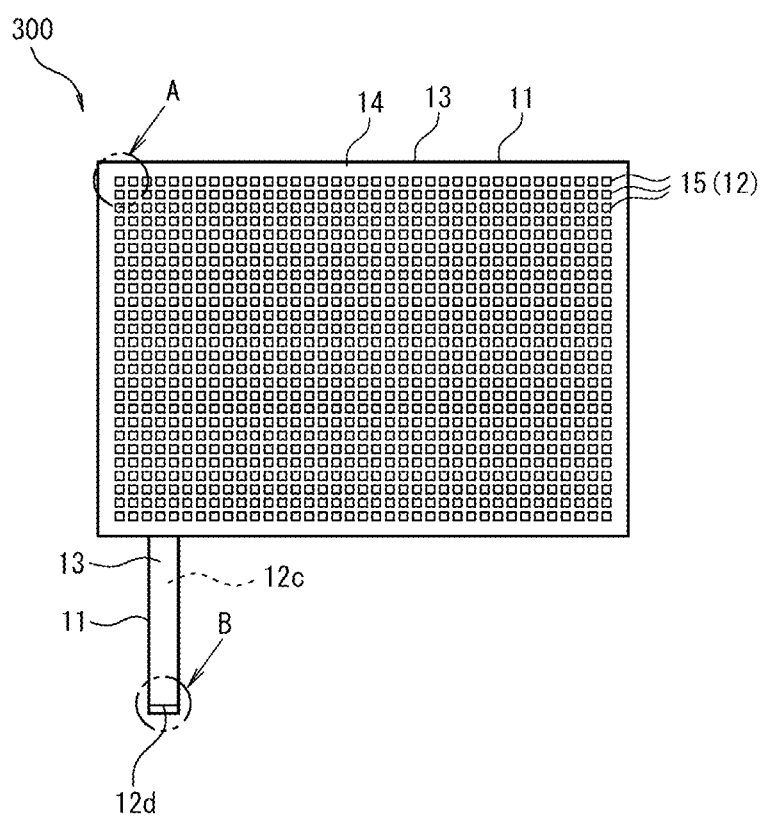
FIG. 5 A plan view illustrating a pressure sensing element according to a second embodiment of this invention.
Figure 6A:
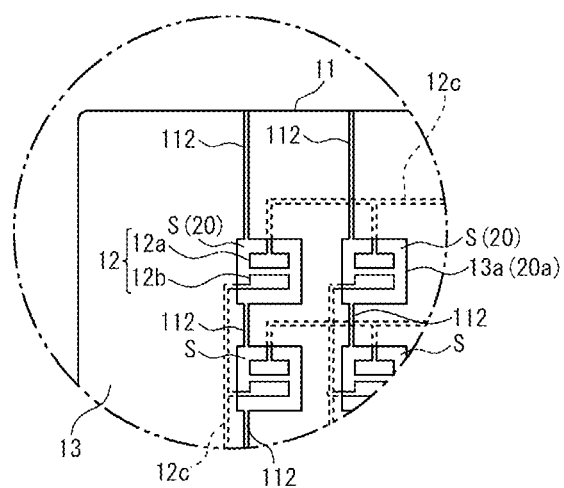
FIG. 6A is a partially enlarged view of part "A" in FIG. 5.
Figure 6B:
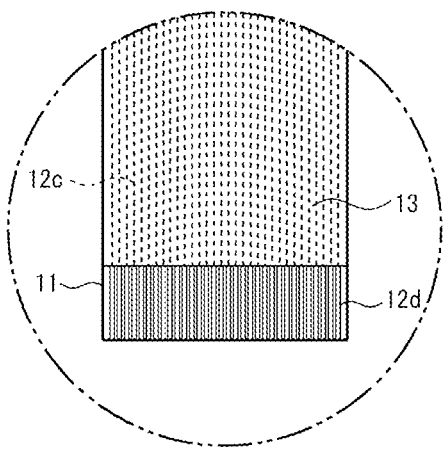
FIG. 6B is a partially enlarged view of part "B" in FIG. 5.
Figure 7A:
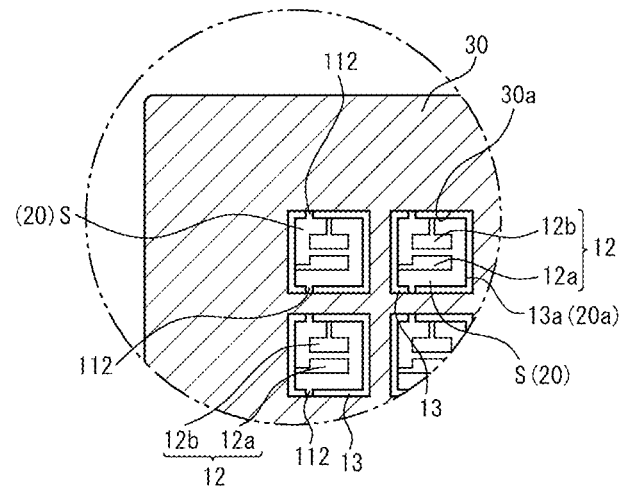
FIG. 7A and FIG. 7B are partially enlarged views of part "A" in FIG. 5, with the pressure sensing film removed.
Figure 7B:
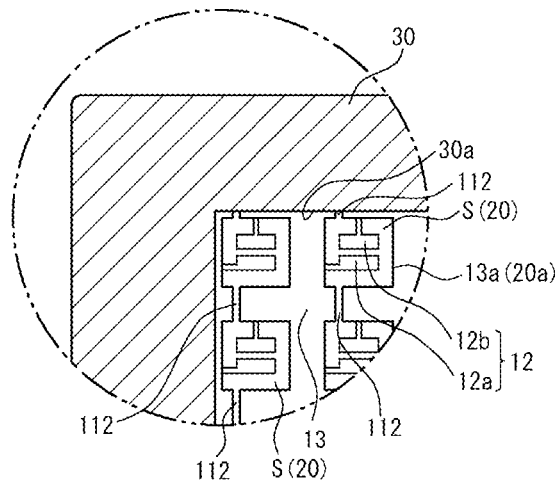
Figure 8:
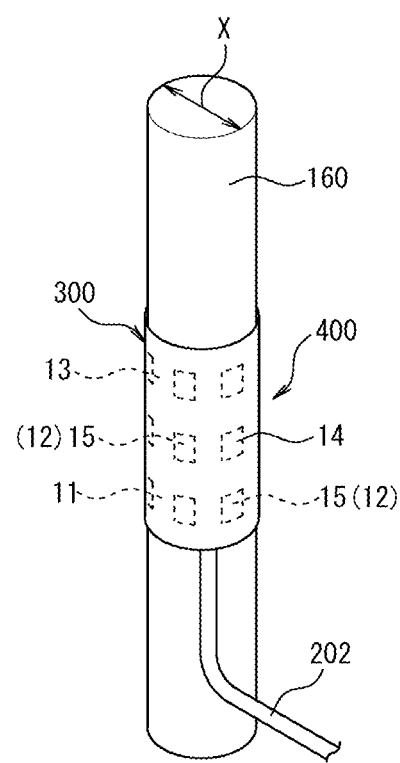
FIG. 8 A perspective view illustrating a pressure sensor having a pressure sensing element mounted on the surface of a cylinder having diameter X.

FIG. 5 is a plan view illustrating the pressure sensing element 300 according to the second embodiment of this invention. FIG. 6A is a partially enlarged view of part "A" in FIG. 5, and FIG. 6B is a partially enlarged view of part "B" in FIG. 5. FIG. 7A and FIG. 7B are partially enlarged views of part "A" in FIG. 5, from which the pressure sensing film 14 has been removed. FIG. 8 is a perspective view illustrating a pressure sensor 400 having the pressure sensing element 300 mounted on the surface of a cylinder 160 having diameter X. The detection unit 210 is not illustrated in FIG. 8. FIG. 9A to FIG. 9D illustrate a pressure sensing element 300 manufactured by the method of manufacturing a pressure sensing element of this invention.

The pressure sensing element 300 is, as illustrated in FIG. 5, a multi-channel type element having a plurality of pressure sensor parts 15 provided on a single support substrate 11. Every single pressure sensor part 15 has the unillustrated sensor electrode 12 and the pressure sensing film 14 opposed thereto. The configuration of the pressure sensor part 15 may be referred to the pressure sensing element 100 of the first embodiment for convenience. In the pressure sensing element 300, the lead wires 12c drawn out from the individual sensor electrodes 12 are connected to the external terminal electrodes 12d. The pressure sensing element 300 is properly configured in the same way as the pressure sensing element 100, except that there are the plurality of pressure sensor parts 15, and that the lead wires 12c and external terminal electrodes 12d are provided corresponded to the plurality of pressure sensor parts 15.

As illustrated in FIG. 6A and FIG. 6B, the pressure sensing element 300 has the plurality of sensor electrodes 12 each having a pair of the first electrode 12a and the second electrode 12b, and there are provided the plurality of pressure sensor parts 15 each configured by a pressure sensing film 14 and a single sensor electrode 12 opposed while placing the opening 20 in between (see FIG. 5). In the pressure sensing element 300, a single pressure sensing film 14 is disposed so as to extend over, and so as to oppose with, the plurality of sensor electrodes 12.

By configuring the plurality of pressure sensor parts 15 by disposing a single pressure sensing film 14 so as to extend over the plurality of sensor electrodes 12, a process load for patterning or alignment of the pressure sensing film 14 may be relieved, and the configuration of the pressure sensing element 300 may be simplified. In addition, film materials are often manufactured according to the standard width, which is as wide as 500 mm, 1000 mm and so on. For this reason, when the array-type pressure sensing element 300 is manufactured, the productivity may dramatically be improved by disposing a single large pressure sensing film 14 so as to oppose with the plurality of sensor electrodes 12, as compared with the case where the pressure sensing films 14 are disposed in an island pattern. In this specification, the "array-type" means a type having a sensor group which is configured by a plurality of sensor electrodes 12 arranged regularly.

The pressure sensing element 300 of this embodiment has difference I, described below, three times or more larger than difference II. For the explanation of differences I, II, FIG. 9D is conveniently referred to.

Difference I is a value calculated by subtracting height H3 of the sensor electrode 12, measured from the support substrate 11, from height H2 of the insulating layer 13 at the aperture end (top aperture end 13a).

Difference II is a value calculated by subtracting height H3 of the sensor electrode 12, measured from the support substrate 11, from height H6 of the insulating layer 13 in a middle part between the adjacent pressure sensor parts 15. Now the middle part means a region between the adjacent pressure sensor parts 15a, 15b (see FIG. 9D) which falls in a valley between the slopes, and specifically means a right center between the pressure sensor parts 15a, 15b.

In the conventional pressure sensing element, the insulating layer has been formed by a film having an almost uniform thickness, so that difference I and difference II have been substantially equal. The insulating layer at around the opening has therefore been substantially flat, also the pressure sensing film disposed conforming to the surface of the insulating layer has therefore been substantially flat, so that the slope 22, as seen in this invention, has not been formed at all. Accordingly, in the conventional pressure sensing element, there was no means for orienting the inclination of the surface of the pressure sensing film towards the first direction. In contrast, in the pressure sensing element 300 of this embodiment, difference I is set three times or more larger than difference II, preferably five times or larger, more preferably seven times or larger, and particularly 10 times or larger. As a consequence, in the pressure sensing element 300 having the plurality of pressure sensor parts 15, the slopes 22 are formed in the insulating layer 13 in the vicinity of the openings 20, so that the pressure sensing film 14 may successfully be stacked thereon.

Note, if difference II is smaller than zero, then such difference II is assumed to zero, and the ratio relative to difference I is calculated.

In the pressure sensing element 300, when measured from the support substrate 11, height H2A of the aperture end (top aperture end 13a) of one pressure sensor part 15 may be different from height H2B of the aperture end (top aperture end 13a) of other pressure sensor part 15. Height H2A and height H2B are referred to FIG. 9D. According to this embodiment, in the array-type pressure sensing element 300, the initial pressure sensing load may be varied between one sensor electrode 12 and other sensor electrode 12. Accordingly, the initial detection sensitivity may be varied among predetermined regions in a single pressure sensing element 300, and thereby modes of use of the pressure sensing element 300 may be expanded.

The pressure sensing element 300 of this embodiment can provide an array-type pressure sensor 400 (see FIG. 8). In this embodiment, a plurality of pressure sensor parts 15 are formed by allowing a plurality of sensor electrodes 12 to oppose with a single pressure sensing film 14. This embodiment, however, shall not preclude that the pressure sensing element of this invention is applied to a pressure sensor in which a plurality of pressure sensor parts 15 are configured by allowing the individual sensor electrodes 12 to oppose with the respective pressure sensing films 14. In other words, the pressure sensing element of this invention is also applicable to the pressure sensor in which the pressure sensing films 14 are arranged in an island pattern corresponding to the individual sensor electrodes 12.

The pressure sensing element 300 has, as illustrated in FIG. 6A, a plurality of sensor electrodes 12 each having the pair of first electrode 12a and the second electrode 12b. Each of the first electrode 12a and the second electrode 12b is respectively connected with the lead wire 12c, through which voltage is applied from a voltage supply unit not illustrated. The pressure sensing film 14, upon externally loaded with pressurizing force, is brought into contact with the sensor electrode 12 to bridge the first electrode 12a and second electrode 12b, and this electrifies the first electrode 12a and the second electrode 12b, and current flows through the lead wire 12.

The distance between every adjacent sensor electrode 12 may be determined depending on applications of the pressure sensing element 300. It may be 1 mm or longer and 10 mm or shorter, for instance. Although FIG. 5 illustrates an exemplary mode wherein the plurality of sensor electrodes 12 forms a regular matrix on the support substrate 11, this embodiment is not limited thereto. The plurality of sensor electrodes 12 may be arranged in a lattice pattern or in a staggered manner, and even randomly.

The pressure sensing element 300 has the adhesion layer 30 which binds the pressure sensing film 14 and the insulating layer 13 (see FIG. 7A and FIG. 7B).

The insulating layer 13 has openings 20 through which the pressure sensing film 14 is opposed to the sensor electrodes 12 while placing the hollow space S in between. In this embodiment, the adhesion layer 30 has apertures 30a. Each aperture 30a contains, in a plan view, the upper aperture 20a of each opening. In other words, in this embodiment, the aperture 30a is larger than the upper aperture 20a of the opening 20 in a plan view, and therefore contains the upper aperture 20a. With such configuration, the adhesive which composes the adhesion layer 30 may be prevented from entering the hollow space S out from the upper aperture 20a.

FIG. 7A illustrates an exemplary mode wherein the opening 20 and the aperture 30a surround each sensor electrode 12. FIG. 7B illustrates a mode wherein one aperture 30a surrounds a plurality (all, for example) of sensor electrodes 12. Inside such single aperture 30a, each sensor electrodes 12 is arranged inside each opening 20.

For example, in the pressure sensor 400 of this embodiment, the pressure sensing element 300 is curved with a radius of curvature 15 mm or smaller. Although depending on the overall design, typically as can be referred to FIG. 2A, the pressure sensing element 300 preferably has a predetermined distance A of 5 µm or longer and 25 µm or shorter, and a distance D5 of 50 µm or longer and 850 µm or shorter. With such configuration, the pressure sensing element 300 may be used while being bent up to a radius of curvature of 15 mm or smaller, further up to a radius of curvature of 10 mm or smaller, and even up to a very small radius of curvature of 7 mm or smaller. While illustrated in FIG. 8 was an exemplary case where the pressure sensor 400 was used on the surface of a simple cylinder, the pressure sensor 400 may also be adaptable to a curved surface of an object with a more complex profile.

Third Embodiment

Next, as a third embodiment of this invention, the method of manufacturing a pressure sensing element of this invention will be explained referring to FIG. 9A, FIG. 9B, FIG. 9C, FIG. 9D and FIG. 10. Although this embodiment will explain a method of manufacturing the pressure sensing element 300, the description may conveniently be referred to as describing the method of manufacturing a single-channel pressure sensing element 100 having only one pressure sensitive part.

Figure 9B:
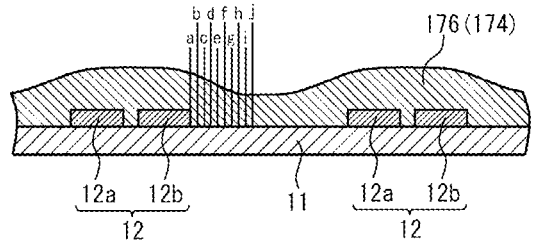
FIG. 9B illustrates the photo-sensitive coating material having been coated over the support substrate.
Figure 9C:
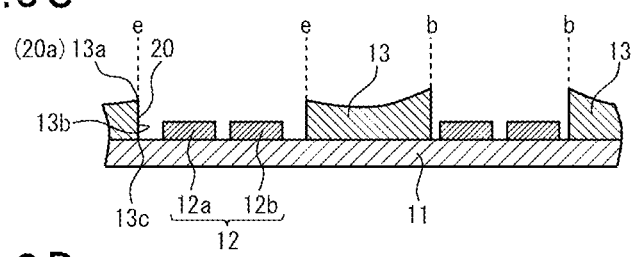
FIG. 9C illustrates an insulating layer having been exposed and developed to have openings formed therein.
Figure 9D:
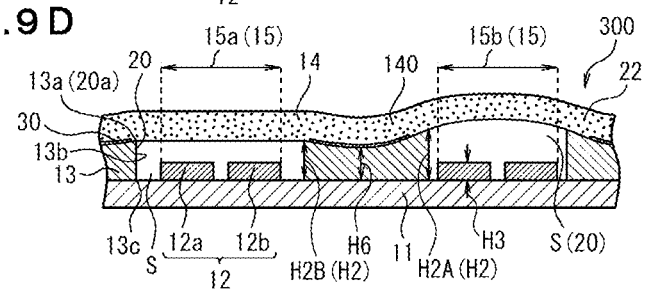
FIG. 9D illustrates a pressure sensing element thus manufactured.
Figure 10:
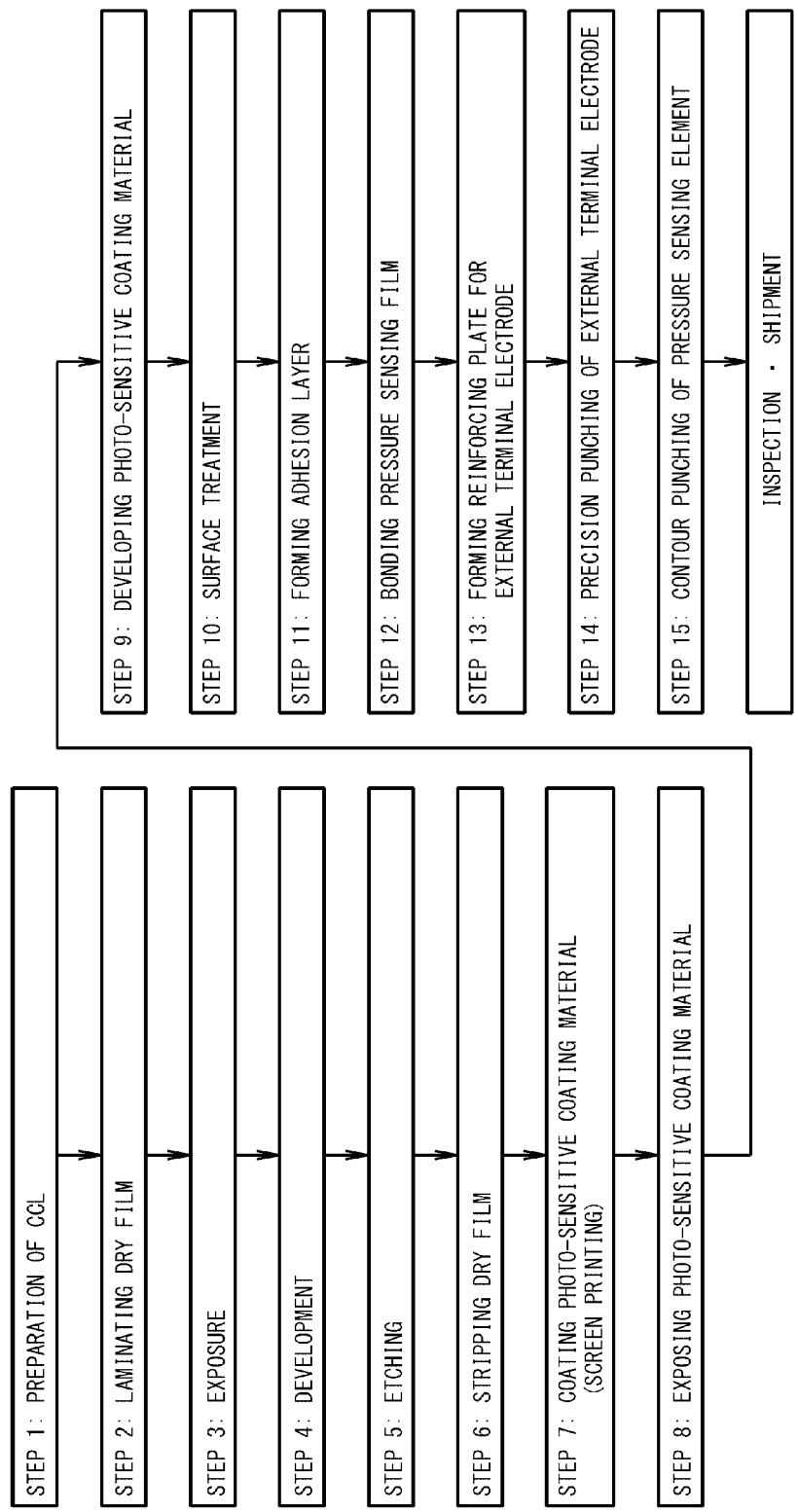
FIG. 10 A flow chart of steps of manufacturing the pressure sensing element according to the third embodiment of this invention.

FIG. 9A to FIG. 9D are an explanatory drawing explaining steps of manufacturing the pressure sensing element according to the third embodiment of this invention. FIG. 9A to FIG. 9D illustrate a cross sectional view taken at a portion where the sensor electrodes 12 are formed, in the direction of normal line of the support substrate 11. FIG. 9A illustrates a step of coating of a photo-sensitive coating material 174 by screen printing over the support substrate 11 having sensor electrodes 12 provided thereto. FIG. 9B illustrates a photo-sensitive coated film 176 formed by coating the photo-sensitive coating material 174 over the support substrate 11. FIG. 9C illustrates the insulating layer 13 having been exposed and developed to have openings 20 formed therein. FIG. 9D illustrates the pressure sensing element 300 manufactured here. FIG. 10 is a flow chart of steps of manufacturing the pressure sensing element according to the third embodiment of this invention.

The method of manufacturing a pressure sensing element of this embodiment (also referred to as this manufacturing method, hereinafter) is a method of manufacturing the pressure sensing element of this invention (pressure sensing element 300), and includes the electrode forming step, the coating step, the insulating layer forming step, and the pressure sensing film forming step. In the electrode forming step, the sensor electrodes 12 are formed at least on one surface of the support substrate 11. In the coating step, the photo-sensitive coating material 174 is coated so as to cover the support substrate 11 and the sensor electrodes 12. In the insulating layer forming step, the photo-sensitive coating material 174 is exposed and developed, to thereby form the insulating layer having formed therein the openings 20 which are partitioned by the aperture wall 13b and the aperture ends (top aperture end 13a and bottom aperture end 13c) and allow therein the sensor electrodes 12 to expose. In the pressure sensing film forming step, the pressure sensing film 14 is formed by placing an electro-conductive resin film over the surface of the insulating layer 13.

In this manufacturing method, the coating step includes a step of coating the photo-sensitive coating material 174 by screen printing. This manufacturing method is characterized in that the insulating layer forming step, successive to the coating step, includes a step of exposing and developing the photo-sensitive coating material 174 according to the guidelines (1) and (2), to thereby form the openings 20 in the insulating layer 13.

According to the guideline (1), the height of the insulating layer 13, measured from the support substrate 11, is increased continuously towards the opening 20.

According to the guideline (2), the in-plane distance (distance D5, see FIG. 2A) between the side wall of the sensor electrode 12, faced to the aperture wall 13b, and the aperture end (top aperture end 13a) is controlled within the range from 50 μm or longer and 850 μm or shorter.

According to this manufacturing method, the pressure sensing element 300 may be manufactured by screen printing and photolithographic technique which are general techniques. In conformity with the guidelines (1) and (2), the pressure sensing element 300 which is successfully prevented from short-circuiting and excellent in the initial detection sensitivity may be manufactured easily.

The pressure sensing element 300 manufactured by this manufacturing method has the slope 22 in the insulating layer 13, so that, the smaller the aperture size of the opening 20 will be, the higher the top aperture end 13a will be, and the wider the aperture size of the opening 20 will be, the lower the top aperture end 13a will be. Accordingly, this manufacturing method allows an easy control of the initial pressure sensing load as described below.

More specifically, the initial pressure sensing load of the first pressure sensing element 300 manufactured according to this manufacturing method is measured. If the initial pressure sensing load is found to be larger than a predetermined value, a second pressure sensing element 300 may be manufactured according to this manufacturing method, by increasing distance D5 described above in the guideline (2) within the above-described range so as to control the initial pressure sensing load.

Alternatively, the initial pressure sensing load of the first pressure sensing element 300 manufactured according to this manufacturing method is measured. If the initial pressure sensing load is found to be smaller than a predetermined value, a second pressure sensing element 300 may be manufactured according to this manufacturing method, by decreasing distance D5 described above in the guideline (2) within the above-described range so as to control the initial pressure sensing load.

Note that the predetermined values in the context of the guideline (1) and the guideline (2) may represent either predetermined range or predetermined value. This manufacturing method encompasses both cases where the predetermined value in the guideline (1) and the predetermined value in the guideline (2) are same, and different.

As described above, according to this manufacturing method, the initial pressure sensing load of the pressure sensing element 300 may be optimized easily. Again according to this manufacturing method, it is no more necessary to preliminarily obtain films with different thicknesses in order to change the height of the top aperture end 13a for the purpose of controlling the initial pressure sensing load, instead only change in distance D5 using a single component will suffice, so that the number of necessary components may be reduced.

Next, this manufacturing method will be detailed referring to FIG. 10. Note, however, that this manufacturing method by no means limit this invention, and shall not preclude that the pressure sensing element of this invention 300 is manufactured by some different method. The steps 1 to 15 below may appropriately be changed in order, partially omitted, or partially modified.

[Step 1] Preparation of CCL

A CCL is prepared. The CCL may suitably be pierced to form a guide hole, in preparation for alignment which may be necessary in the succeeding steps. The CCL has a copper foil formed over the support substrate 11.

The steps 1 to 6 represent an exemplary mode of the electrode forming step.

[Step 2] Step of Laminating Dry Film

The above-prepared CCL is rinsed with an acid, and is laminated with a dry film by roll lamination.

[Step 3] Exposure Step

The CCL obtained in the step 2 is placed in an exposure apparatus, and exposed according to patterns of the sensor electrodes 12, the lead wires 12c, and the external terminal electrodes 12d.

[Step 4] Development Step

The exposed CCL is sent to a developing machine to form a pattern. The developing solution is generally a weak alkali solution. The dry film pattern remained on the CCL after the development serves as an etching resist in the etching step described later. After the etching resist is patterned by the development, the CCL and the etching resist are optionally rinsed with water so as to remove the developing solution adhered thereto.

[Step 5] Etching Step

The CCL, having formed thereon the etching resist composed of the patterned dry film, is then etched. The etching solution used here is generally a copper chloride containing solution, but is arbitrarily selectable from chemical solutions capable of etching the Cu foil, without special limitation. By the etching, the sensor electrodes 12, the lead wires 12c, and the external terminal electrode 12d are formed according to predetermined patterns in the CCL. After completion of this step, the dry film remains on the individual patterns. The sensor electrodes 12 include the first electrode 12a and the second electrode 12b.

[Step 6] Step of Stripping Dry Film

After the etching step, the dry film remaining on the individual patterns is stripped. The stripping is generally proceeded by a technique of swelling and then lifting off the dry film using a weak-alkaline stripping solution. After the stripping of the dry film, the CCL is rinsed with water, and subjected to rustproofing for protecting the exposed Cu pattern. In this way, the sensor electrodes 12, and the lead wires 12*c* are formed in the CCL.

[Step 7] Step of Coating Photo-Sensitive Coating Material

Steps 7 to 9 represent an exemplary mode of the coating step, and the step of forming insulating layer of this manufacturing method, for which FIG. 9A to FIG. 9C are conveniently referred to.

In step 7, the photo-sensitive coated film 176 is formed over the CCL obtained in step 6. More specifically, as illustrated in FIG. 9A, a screen plate 172 is placed on the CCL so as to cover the support substrate 11, and the sensor electrodes 12. The screen plate 172 rises up on the sensor electrodes 12, and lands on the support substrate 11 approximately 1 mm away from the sensor electrode 12. A predetermined thickness of the photo-sensitive coating material 174 is formed using a squeegee 170, followed by drying, to form the photo-sensitive coated film 176 (FIG. 9B). The photo-sensitive coated film 176 is thickened at around the portion where the sensor electrodes 12 are formed, and continuously thinned towards the direction away from the sensor electrodes 12.

The screen plate 172 preferably used here is exemplified by a polyester mesh having a mesh count of #120 (general commercial product), and a 3D-woven stainless steel mesh (3D-165-126, from Asada Mesh Co., Ltd.) having a mesh count of #165, but not limited thereto. It is also preferable to prebake the photo-sensitive coated film 176, after formed, just enough to smooth out the tuck on the surface of the photo-sensitive coated film 176. It is also preferable to control the viscosity of the photo-sensitive coating material 174, or timing of exposure, so that the photo-sensitive coating material 174 will not be leveled, and thereby the photo-sensitive coated film 176 will not be planarized.

[Step 8] Step of Exposing Photo-Sensitive Coating Material

The thus formed the photo-sensitive coated film 176 is exposed to light selectively in the region other than the openings 20. By the exposure of light suited to the exposure sensitivity of the photo-sensitive coating material, only the portion exposed to light is photo-polymerized.

In this process, as illustrated in FIG. 9B, by selecting position "a", on the edge of the sensor electrode 12, or a position at around position "a", as the boundary of exposure range, the top aperture end 13*a* (see FIG. 9D) will become high. Meanwhile, by selecting position "j", or a position at around position "j", as the boundary of exposure range, the top aperture end 13*a* (see FIG. 9D) will become low. By controlling the boundary of exposure range, distance D5 explained in the first embodiment or the second embodiment may be set to 50 μm or longer and 850 μm or shorter, and predetermined distance A may be set to 5 μm or longer and 25 μm or shorter. In this exposure step, a vent hole 112 may optionally be formed together with the openings 20.

In the exposure step, as illustrated in FIG. 9C, the aperture size of the openings 20 may be varied by setting different exposure ranges for each of the adjacent sensor electrodes 12. By varying the aperture size of the openings 20, the height of the top aperture end 13*a* may be varied. Such variation in the exposure range for the individual sensor electrodes 12 may be given easily, based on the design of an exposure mask. More specifically, position "b" was selected as the boundary of exposure range at around the sensor electrode 12 on the right hand side of FIG. 9B, meanwhile position "e" was selected as the boundary of exposure range at around the sensor electrode 12 on the left hand side of the drawing.

[Step 9] Step of Developing Photo-Sensitive Coating Material

The product is developed using a weak alkali solution in order to selectively remove the unexposed region in step 8 (that is, the region where the openings 20 are formed). As a consequence, the openings 20 are formed in the insulating layer 13, and thereby the sensor electrodes 12 expose inside the openings 20. Height H2 of the top aperture end 13*a* of the insulating layer 13, measured from the support substrate 11, is larger than height H3 of the sensor electrode 12. The development may be followed by additional baking at a predetermined temperature for a predetermined time, for the purpose of improving the strength of the insulating layer 13, making use of property of the photo-sensitive coating material 174.

As described above, in step 8, the boundary of exposure range was varied respectively for the two adjacent areas around the sensor electrodes 12. Accordingly, the height of top aperture end 13*a*, faced to the sensor electrode 12 illustrated on the right hand side of FIG. 9C, became larger than the height of the top aperture end 13*a* faced to the sensor electrode 12 illustrated on the left hand side of the drawing.

[Step 10] Surface Treatment Step

Partial regions of the sensor electrodes 12, the lead wires 12*c*, and the external terminal electrodes 12*d* provided on the support substrate 11, which are exposed without being covered with the insulating layer 13, are subjected to surface treatment by Ni/Au plating. Either electroplating or electroless plating is conveniently selectable for the plating.

[Step 11] Step of Forming Adhesion Layer

Next, the adhesion layer 30 is formed conforming to the geometry of the insulating layer 13. For example, the adhesion layer 30 may be formed by preparing an adhesive sheet having been punched out at portions corresponded to the individual openings 20, and by laminating it onto the surface of the insulating layer 13, while being aligned with reference to the openings 20. Alternatively, a screen plate is aligned to the insulating layer 13 having the openings 20 formed therein, and the adhesive is coated on the insulating layer 13 by a printing means such as screen printing, to thereby form the adhesion layer 30. Still alternatively, an adhesive sheet having been punched out at portions corresponded to the individual openings 20 may be laminated with the pressure sensing film 14 to form the adhesion layer 30, and the obtained stack may be bonded to the insulating layer 30 while placing the adhesion layer 30 in between as described later. In all cases, the adhesion layer 30 will not reach the top aperture end 13*a*.

[Step 12] Step of Bonding Pressure Sensing Film

Step 12 represents an exemplary mode of a step of manufacturing the pressure sensing film, in this manufacturing method. In step 12, the pressure sensing film 14 is bonded to the surface of the insulating layer 13. Typically by using a vacuum press apparatus generally used for manufacture of flexible printed circuit board (FPC), and by press-bonding the insulating layer 13 and the pressure sensing film 14 under heating in vacuo, while placing the adhesion layer 30 in between, they may be successfully bonded while preventing air from being entrained between the layers. In this way, the pressure sensing film 14 is bonded to the insulating layer 13, in the region other than the region corresponded to the openings 20. Since, height H3 of the sensor electrode 12 is lower than height H2 of the top aperture end 13*a*, when measured from the support substrate 11, so that the sensor electrode 12 and the pressure sensing film 14 are kept apart in the initial state where no external pressure is applied, and are not short-circuited.

[Step 13] Step of Forming Reinforcing Plate for External Terminal Electrode

For the external terminal electrodes 12d of the pressure sensing element 300 intended to be plugged or unplugged to or from a connector, or to be used in a bonded form with an anisotropic conductive film (ACF), the steps below are optionally implemented. More specifically, in order to make the external terminal electrodes 12d appropriately rigid, a reinforcing plate (not illustrated) is formed on the external terminal electrodes 12d. The reinforcing plate is generally composed of a plate made of metal such as stainless steel or aluminum, or a film made of polyimide or polyethylene terephthalate, having a desired thickness, and is laminated with the external terminal electrodes 12d using a tacky agent or adhesive.

[Step 14] Step of Precision Punching of External Terminal Electrode

In many cases, the external terminal electrodes 12d of the pressure sensing element 300 is generally connected to external board or instrument through plugging or unplugging of a connector, or bonding with ACF. Accordingly, a high level of dimensional accuracy is often required for the punching which determines profile of the portion contributive to the connection. More specifically, the punching is implemented using a precisely-machined die, to satisfy a level of dimensional accuracy required for the external terminal electrodes 12d.

[Step 15] Step of Contour Punching of Pressure Sensing Element

Precision punching of the external terminal electrodes 12d is followed by a step of contour punching for determining overall contour of the pressure sensing element 300.

The pressure sensing element 300 is manufactured by the steps 1 to 15 described above. The thus manufactured pressure sensing element 300 is then checked in terms of dimension of the individual portions, conduction performance of the sensor electrodes 12 and the lead wires 12c, and pressure-sensitive resistivity characteristic, and those satisfied certain standards are shipped as accepted products. Alternatively, the pressure sensing element 300 obtained above may be electrically connected with the detection unit 210 to manufacture the pressure sensor 400. If the pressure sensing element 300 manufactured as described above has the sensor electrodes 12 and the lead wires 12c provided only on one surface thereof, the CCL with the support substrate 11 may be processed in the form of roll which is passed through steps 1 to 15 form.

The pressure sensing element 300 thus manufactured is shown in FIG. 9D, in which a pressure sensor part 15a (15) on the left hand side of the drawing has a larger aperture size of the opening 20, and a lower height of the top aperture end 13a, than those of the pressure sensor part 15b (15) on the right hand side of the drawing. Accordingly, the pressure sensor part 15a (15) has an initial pressure sensing load smaller than that of the pressure sensor part 15b (15).

Having described above the first embodiment to the third embodiment of this invention, this invention is not limited to the above-described embodiments, and may include various modifications and improved modes so long as the purpose of this invention will successfully be achieved.

For example, while all embodiments described above dealt with the exemplary case having the sensor electrodes 12 on one surface of the support substrate 11, this invention is not limited thereto. This invention encompasses the mode having the sensor electrodes 12 and the pressure sensing film 14 provided on both surfaces of the support substrate 11. This invention is again not limited to the case where the film-type support substrate 11 is used as the substrate on which the sensor electrodes 12 are formed. This invention can embody the pressure sensing element 300 on various types of substrates capable of supporting the sensor electrode(s) 12, and allowing thereon formation of the insulating layer 13 and pressure sensing film 14 in a stacked manner.

Advantageous Effects of Invention

The pressure sensor of this invention is suitable for applications where low measurement errors and high resolution are required, such as measurement of pressure distribution over a flat surface, or various curved surfaces including spherical surface (in particular, flexible curved surface with a small curvature, and possibly causing thereon dynamic changes in the curvature). The pressure sensor of this invention is also suitable for applications where pressure distribution is measured by an instrument having a relatively large area.

For example, objects to be measured by the pressure sensor of this invention include surfaces of human body or robot's body, or surfaces of objects in contact therewith. Diversified fields of application include tactile sensor for hand, finger or thenar (input device for information equipment, a device for detecting massive feeling felt by hand which grasps something), tactile sensor for robot's arm or artificial arm, measurement of surface pressure distribution of chair or bed (including device for developing and evaluating medical and assistive devices), and measurement of pressure distribution over torso and limbs (including applicable fields of medical treatment, motion measurement and apparel).

For example, the pressure sensor 400 of this invention may be disposed over a part, or entire portion, of an area modeled on the human hand, to implement a hand-shaped, or glove-type pressure sensor. Even a pressure sensor 200, having the pressure sensing element 100 composed of a single sensor electrode 12, may be used while being placed on a surface with a complex texture, in the same way as for the pressure sensor 400.

EXAMPLES

Figure 11:
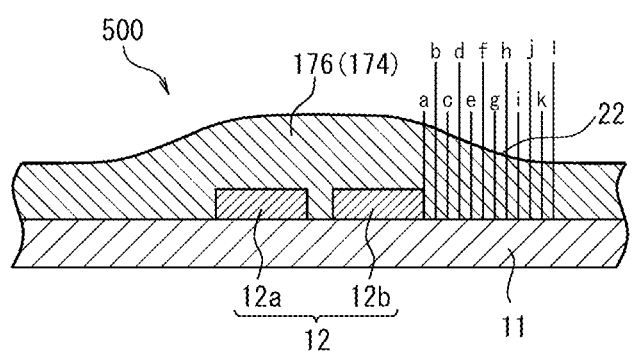
FIG. 11 An explanatory drawing illustrating a printing work used for Examples of this invention and Comparative Examples.

Examples and Comparative Examples of this invention will be illustrated below. The individual Examples and Comparative Examples were manufactured according to the configuration of the pressure sensor 200 having the single-channel pressure sensing element 100 illustrated in FIG. 1. Note that "height" in Examples means height measured from the surface of the support substrate 11, on which the sensor electrodes 12 are formed, unless otherwise specifically noted. In this Example, FIG. 1, FIG. 2A, FIG. 2B, FIG. 9A, FIG. 9B, FIG. 9C, FIG. 9D and FIG. 11 are conveniently referred to. FIG. 11 is an explanatory drawing illustrating a printing work 500, having formed thereon the photo-sensitive coated film 176, used for Examples of this invention and Comparative Examples.

First, as a member commonly used for the individual Examples and Comparative Examples, the support substrate 11 (referred to as "printing work", hereinafter) having formed thereon the sensor electrode 12 was manufactured. A polyimide film (25 µm thick) was used as the support substrate 11, on which the sensor electrode 12 having a pair of the first electrode 12a and the second electrode 12b, the lead wire 12c, and the external terminal electrode 12d were formed. The first electrode 12a and the second electrode 12b were 19 μm high.

On the surface of the above-manufactured printing work, and on the side thereof the sensor electrode 12 is provided, the photo-sensitive coated film 176 was formed by screen printing as described below. More specifically, on the top surface of the printing work, the screen plate 172 which is a 120-mesh (#120) polyester mesh was placed so as to be mounted on the sensor electrode 12, and so as to be landed on the surface of the support substrate 11 around the sensor electrode 12 (see FIG. 9A). The squeegee 170 was moved along the screen plate 172 so as to coat the photo-sensitive coating material 174 onto the printing work, and the screen plate 172 was then removed, to thereby obtain the printing work having the photo-sensitive coated film 176 formed thereon by coating the photo-sensitive coating material 174 (see FIG. 11).

[Measurement of Height of Photo-Sensitive Coated Film 176]

The above-obtained printing work having the photo-sensitive coated film 176 was embedded in an acrylic resin to thereby manufacture a test piece. The test piece was then sliced in the direction of normal line of the support substrate 11, at individual positions "a" to "l" indicated in FIG. 11, and the cross sections were polished to give the individual samples to be measured. Values of distance D5 measured from the sensor electrode 12 (side face of the second electrode 12b) to the individual positions "a" to "l" were summarized in Table 1.

The cross section of each sample to be measured was observed under an optical microscope with a critical dimension measurement function, the thickness of the photo-sensitive coated film 176 was measured to the first decimal place, and the measured value was rounded off to determine the height of the photo-sensitive coated film 176. For the measurement of thickness of the film, 30 samples to be measured were prepared for every predetermined position, and the thickness of the film was measured at two points in every sample to be measured, totaling 60 points. The height of the photo-sensitive coated film 176 at positions "a" to "l" (averages of the rounded-off values of measured thickness collected from 60 points), and distance A determined by subtracting the thickness of the sensor electrode (19 μm) from the height are summarized in Table 1.

[Table 1]

TABLE 1

| | | Comparative Example 1 | Example 1 | Example 2 | Example 3 | Example 4 | Example 5 | Example 6 | Example 7 | Example 8 | Example 9 | Comparative Example 2 | Comparative Example 3 |
|---|---|---|---|---|---|---|---|---|---|---|---|---|---|
| Position | | a | b | c | d | e | f | g | h | i | j | k | l |
| Distance D5 between sensor electrode 12 and top aperature end 13a (μm) | | 0 | 50 | 150 | 250 | 350 | 450 | 550 | 650 | 750 | 850 | 950 | 1050 |
| Height of sesor electrode 12 (μm) | | | | | | | 19 | | | | | | |
| Height of photo-sensitive coated film 176 (μm) | Maximum | 46 | 43 | 41 | 40 | 38 | 35 | 32 | 30 | 27 | 25 | 23 | 22 |
| | Average | 45 | 43 | 39 | 39 | 37 | 35 | 30 | 29 | 26 | 25 | 23 | 21 |
| | Minimum | 45 | 42 | 39 | 37 | 37 | 34 | 30 | 27 | 24 | 24 | 22 | 21 |
| Difference between height of photo-sensitive coated film 176 and height of sensor electrode 12 (distance A) (μm) | Maximum | 27 | 24 | 22 | 21 | 19 | 16 | 13 | 11 | 8 | 6 | 4 | 3 |
| | Average | 26 | 24 | 20 | 20 | 18 | 16 | 11 | 10 | 7 | 6 | 4 | 2 |
| | Minimum | 26 | 23 | 20 | 18 | 18 | 15 | 11 | 8 | 5 | 5 | 3 | 2 |

As summarized in Table 1, the height of the photo-sensitive coated film 176 was found to continuously increase from position "l" towards position "a". In other words, the height of the photo-sensitive coated film 176 was found to continuously increase from the region having no sensor electrode 12 formed therein, towards the region having the sensor electrode 12 formed therein. In this way, it was confirmed that the slope 22 which upwardly inclines towards the sensor electrode 12 was formed in the photo-sensitive coated film 176, in the vicinity of the sensor electrode 12. It was also confirmed that variation in the thickness at each position was within 3 μm, proving a good dimensional stability. Accordingly, the dimension of the opening 20 may be determined easily by finding the relation between distance A and distance D5 referable to FIG. 2A.

Next, the opening 20 was formed by exposure and development, so as to locate the top aperture end 13a respectively at position "a" to position "l" illustrated in FIG. 11, respectively for Examples and Comparative Examples, to thereby form the insulating layer 13, and thereon the adhesion layer 30, and the pressure sensing film 14 were formed to obtain the pressure sensing element 100. The thus-obtained pressure sensing element 100 was connected with the detection unit 210, to thereby obtain the pressure sensor 200 having a basic configuration. The first electrode 12a and the second electrode 12b were set to have a height of 19 µm, a line width of 1000 µm, and a distance between them of 100 µm. The lead wire 12c was 13 µm high, and 100 µm wide. In the individual Examples and Comparative Examples, area size (see longitudinal dimension W1 and transverse dimension W2 in FIG. 1) of one sensor electrode 12, distance D5 (see FIG. 2A) between the sensor electrode 12 and the top aperture end 13a, and area size of the opening 20 (see longitudinal dimension W3 and transverse dimension W4 in FIG. 1) were measured. Results were summarized in Table 2.

[Table 2]

TABLE 2

|  | Position | Area size of sensor electrode 12 W 1 * W 2 (mm) | Distance D5 between sensor electrode 12 and top aperture end 13a (µ m) | Area size of opening 20 W 3 * W 4 (mm) |
|---|---|---|---|---|
| Comparative Example 1 | a | 2.50 * 4.00 | 0 | 2.50 * 4.00 |
| Example 1 | b |  | 50 | 2.55 * 4.05 |
| Example 2 | c |  | 150 | 2.65 * 4.15 |
| Example 3 | d |  | 250 | 2.75 * 4.25 |
| Example 4 | e |  | 350 | 2.85 * 4.35 |
| Example 5 | f |  | 450 | 2.95 * 4.45 |
| Example 6 | g |  | 550 | 3.05 * 4.55 |
| Example 7 | h |  | 650 | 3.15 * 4.65 |
| Example 8 | i |  | 750 | 3.25 * 4.75 |
| Example 9 | j |  | 850 | 3.35 * 4.85 |
| Comparative Example 2 | k |  | 950 | 3.45 * 4.95 |
| Comparative Example 3 | l |  | 1050 | 3.53 * 5.05 |

The pressure sensors 200 of Examples and Comparative Examples obtained above were subjected to evaluation of pressure sensing characteristics described below. Five samples were prepared and evaluated for every Example and every Comparative Example. Minimum values and maximum values, which were obtained from every five samples in evaluation of initial detection sensitivity and evaluation of detection sensitivity under large load, described later, are summarized in Table 3. In the short-circuit test described later, the pressure sensor 200 was rated as "not observed" if short-circuiting was not observed for all of five samples, and rated as "observed" if short-circuiting was observed in any one of five samples. Results of the evaluations are summarized in Table 3.

Evaluation of Pressure Sensing Characteristics:

[Evaluation of Initial Pressure Sensing Load]

Each of the pressure sensors 200 of Examples and Comparative Examples was placed on a flat surface, and the pressure sensor part 15 was gradually loaded from the outside of the pressure sensing film 14. The load under which electric conduction is initially detected was determined as initial pressure sensing load (N).

[Evaluation of Detection Sensitivity Under Large Load]

Each of the pressure sensors 200 of Examples, Comparative Examples, and Reference Example was placed on a flat surface, and the pressure sensor part 15 having an area of 4 mm$^2$ was loaded with a load of 1.1 MPa (112.5 gf/mm$^2$), under which the resistivity ($\Omega$) was measured.

[Short-Circuit Test]

Each of the pressure sensors 200 of Examples and Comparative Example was wound around a 10 mm diameter glass rod, and occurrence of short-circuit was checked without externally loading the pressure sensor part 15 (i.e., in the initial state).

[Table 3]

TABLE 3

|  |  |  | Comparative Example 1 | Example 1 | Example 2 | Example 3 | Example 4 | Example 5 | Example 6 | Example 7 | Example 8 | Example 9 | Comparative Example 2 | Comparative Example 3 |
|---|---|---|---|---|---|---|---|---|---|---|---|---|---|---|
|  | Position |  | a | b | c | d | e | f | g | h | i | j | k | l |
|  | Distance D5 between sensor electrode 12 and top aperture end 13a (µm) |  | 0 | 50 | 150 | 250 | 350 | 450 | 550 | 650 | 750 | 850 | 950 | 1050 |
| Evaluation of pressure sensing characteristics | Initial pressure sensing load (N) | Maximum | 0.58 | 0.46 | 0.43 | 0.39 | 0.37 | 0.33 | 0.25 | 0.24 | 0.19 | 0.17 | 0.14 | Observed under zero load |
|  |  | Minimum | 0.47 | 0.40 | 0.38 | 0.32 | 0.32 | 0.27 | 0.20 | 0.19 | 0.16 | 0.13 | 0.11 |  |
|  | Sensor resistivity under large load ($\Omega$) | Maximum | 1920 | 1788 | 1592 | 1523 | 1501 | 1402 | 1347 | 1167 | 897 | 743 | 711 | — |
|  |  | Minimum | 1911 | 1779 | 1576 | 1511 | 1478 | 1356 | 1287 | 1045 | 822 | 701 | 688 |  |
|  | Short-circuiting in bent state ($\phi$ 10 mm) |  | Not observed | Not observed | Not observed | Not observed | Not observed | Not observed | Not observed | Not observed | Not observed | Not observed | Observed under zero load | Observed under zero load |
| Status of opening 20 |  |  | Development failure | No problem | No problem | No problem | No problem | No problem | No problem | No problem | No problem | No problem | No problem | No problem |

It was confirmed from Table 3 that each of the pressure sensors 200 of Examples and Comparative Examples showed the initial pressure sensing load in the range from 0.1 N or larger and 0.7 N or smaller, and the sensor resistivity under large load in the range from 500Ω or larger and 2500Ω or smaller, proving good pressure sensing characteristics.

Comparative Example 1, having a distance D5 of zero, was found to show development failure, due to misalignment of exposure in the step of forming the insulating layer 13.

In the short-circuit test, short-circuiting was not observed for all Examples. In contrast, Comparative Examples 2 and 3 showed short-circuiting in the initial bent state.

The embodiments also encompasses the technical spirits described below.

(1) A pressure sensing element which includes:
a support substrate;
a sensor electrode supported by the support substrate;
a pressure sensing film functionalized to be electro-conductive, at least in a portion thereof faced to the sensor electrode; and
an insulating layer which keeps the sensor electrode and the pressure sensing film apart from each other by a predetermined distance, and has formed therein an opening in which the sensor electrode is exposed to the pressure sensing film,
the insulating layer having an aperture wall which partitions the opening, and an aperture end faced to the pressure sensing film, and
the insulating layer being increased in height, measured from the support substrate, continuously towards the opening.

(2) The pressure sensing element according to (1),
wherein the height of the pressure sensing film, measured from the support substrate, is larger in a portion faced to the center of the opening, than in a portion faced to the aperture end.

(3) The pressure sensing element according to (1) or (2),
wherein the aperture end is rounded.

(4) The pressure sensing element according to any one of (1) to (3),
wherein the in-plane distance between the side wall of the sensor electrode, faced to the aperture wall, and the aperture end is 50 μm or longer and 850 μm or shorter.

(5) The pressure sensing element according to any one of (1) to (4),
wherein the difference of height, measured from the support substrate, between the aperture end and the sensor electrode is 5 μm or larger and 25 μm or smaller.

(6) The pressure sensing element according to any one of (1) to (5),
wherein the surface of the insulating layer, faced to the pressure sensing film, and the pressure sensing film are fixed to each other while placing an adhesion layer in between, and,
the surface of the insulating layer, faced to the support substrate, is fixed to the support substrate without placing an adhesion layer in between.

(7) The pressure sensing element according to any one of (1) to (6),
wherein the pressure sensing film is a resin film containing a carbon particle, and
the pressure sensing film is functionalized to be electro-conductive by the carbon particle.

(8) The pressure sensing element according to any one of (1) to (7), which includes
a plurality of the sensor electrodes each having a pair of first electrode and second electrode, and
a plurality of pressure sensor parts each configured by the pressure sensing film and one sensor electrode opposed to each other while placing the opening in between, and
a single sheet of the pressure sensing film is opposed over the plurality of sensor electrodes.

(9) The pressure sensing element according to (8),
wherein difference I, calculated by subtracting the height of the sensor electrode, measured from the support substrate, from the height of the insulating layer at the aperture end,
is three times or more larger than difference II, calculated by subtracting the height of the sensor electrode, measured from the support substrate, from the height of the insulating layer in a middle portion between the adjacent pressure sensor parts.

(10) The pressure sensing element according to (8) or (9),
wherein the height of the aperture end, measured from the support substrate, in one pressure sensor part is different from the height of the aperture end in other pressure sensor part.

(11) A pressure sensor which includes:
the pressure sensing element described in any one of (1) to (10); and
a detection unit which is electrically connected to the pressure sensing element and detects contact resistance between the pressure sensing film and the sensor electrode.

(12) The pressure sensor according to (11),
wherein the pressure sensing element is curved with a radius of curvature of 15 mm or smaller.

(13) A method of manufacturing a pressure sensing element described in any one of (1) to (10), the method includes:
an electrode forming step, forming a sensor electrode on at least one surface of a support substrate;
a coating step, coating a photo-sensitive coating material so as to cover the support substrate and the sensor electrode;
an insulating layer forming step, forming an insulating layer by exposing and developing the photo-sensitive coating material, the insulating layer having an opening which is partitioned by an aperture wall and an aperture end, and allows therein the sensor electrode to expose; and
a pressure sensing film forming step, forming a pressure sensing film by placing a resin film, functionalized to be electro-conductive, so as to blanket the insulating layer,
the coating step further includes a step of coating the photo-sensitive coating material by a screen printing technique, and
the insulating layer forming step, succeeding to the coating step, further includes exposing and developing the photo-sensitive coating material, according to the guidelines (1) and (2) below, to thereby form the opening in the insulating layer:
guideline (1): increasing the height of the insulating layer, measured from the support substrate, continuously towards the opening; and
guideline (2): controlling the in-plane distance between the side wall of the sensor electrode, faced to the aperture wall, and the aperture end in the range from 50 μm or longer and 850 μm or shorter.

(14) The method of manufacturing a pressure sensing element according to claim 13,
wherein if an initial pressure sensing load of a first pressure sensing element, manufactured by the method of manufacturing a pressure sensing element described in claim 13, was measured and found to be larger than a predetermined value, controlling the initial pressure sensing load, by manufacturing a second pressure sensing element, having the distance according to the guideline (2) increased within the above-described range, according to the method of manufacturing a pressure sensing element.

(15) The method of manufacturing a pressure sensing element according to claim 13, wherein if an initial pressure sensing load of a first pressure sensing element, manufactured by the method of manufacturing a pressure sensing element described in claim 13, was measured and found to be smaller than a predetermined value, controlling the initial pressure sensing load, by manufacturing a second pressure sensing element, having the distance according to the guideline (2) decreased within the above-described range, according to the method of manufacturing a pressure sensing element.

The invention claimed is:

1. A pressure sensing element comprising:
    a support substrate;
    a sensor electrode supported by the support substrate;
    a pressure sensing film functionalized to be electro-conductive, at least in a portion thereof faced to the sensor electrode; and
    an insulating layer which keeps the sensor electrode and the pressure sensing film apart from each other by a predetermined distance, and has formed therein an opening in which the sensor electrode is exposed to the pressure sensing film,
    the insulating layer having an aperture wall which partitions the opening, and an aperture end faced to the pressure sensing film, and
    the insulating layer being increased in height, measured from the support substrate, continuously towards the opening.

2. The pressure sensing element according to claim 1,
    wherein the height of the pressure sensing film, measured from the support substrate, is larger in a portion faced to the center of the opening, than in a portion faced to the aperture end.

3. The pressure sensing element according to claim 2, wherein the aperture end is rounded.

4. The pressure sensing element according to claim 1, wherein the aperture end is rounded.

5. The pressure sensing element according to claim 1,
    wherein the in-plane distance between the side wall of the sensor electrode, faced to the aperture wall, and the aperture end is 50 μm or longer and 850 μm or shorter.

6. The pressure sensing element according to claim 1,
    wherein the difference of height, measured from the support substrate, between the aperture end and the sensor electrode is 5 μm or larger and 25 μm or smaller.

7. The pressure sensing element according to claim 1,
    wherein the surface of the insulating layer, faced to the pressure sensing film, and the pressure sensing film are fixed to each other while placing an adhesion layer in between, and,
    the surface of the insulating layer, faced to the support substrate, is fixed to the support substrate without placing an adhesion layer in between.

8. The pressure sensing element according to claim 1,
    wherein the pressure sensing film is a resin film containing a carbon particle, and
    the pressure sensing film is functionalized to be electro-conductive by the carbon particle.

9. The pressure sensing element according to claim 1, comprising:
    a plurality of the sensor electrodes each having a pair of first electrode and second electrode; and
    a plurality of pressure sensor parts each configured by the pressure sensing film and one sensor electrode opposed to each other while placing the opening in between, and
    a single sheet of the pressure sensing film is opposed over the plurality of sensor electrodes.

10. The pressure sensing element according to claim 9,
    wherein difference I, calculated by subtracting the height of the sensor electrode, measured from the support substrate, from the height of the insulating layer at the aperture end,
    is three times or more larger than difference II, calculated by subtracting the height of the sensor electrode, measured from the support substrate, from the height of the insulating layer in a middle portion between the adjacent pressure sensor parts.

11. The pressure sensing element according to claim 10,
    wherein the height of the opening, measured from the support substrate, in one pressure sensor part is different from the height of the aperture end in other pressure sensor part.

12. The pressure sensing element according to claim 9,
    wherein the height of the opening, measured from the support substrate, in one pressure sensor part is different from the height of the aperture end in other pressure sensor part.

13. The pressure sensing element according to claim 1, further comprising: a detection unit which is electrically connected to the pressure sensing element and detects contact resistance between the pressure sensing film and the sensor electrode.

14. The pressure sensing element according to claim 13, wherein the pressure sensing element is curved with a radius of curvature of 15 mm or smaller.

* * * * *